US010745679B2

(12) United States Patent
Persillon et al.

(10) Patent No.: US 10,745,679 B2
(45) Date of Patent: Aug. 18, 2020

(54) VARIANTS OF EXOGLUCANASES HAVING IMPROVED ACTIVITY AND USES THEREOF

(71) Applicants: IFP Energies nouvelles, Rueil Malmaison (FR); Proteus, Longjumeau (FR); CENTRE NATIONAL DE LA RECHERCHE SCIENTIFIQUE—CNRS—, Paris (FR)

(72) Inventors: Cecile Persillon, Nimes (FR); Christophe Ullmann, Nimes (FR); Celine Ayrinhac, Domessargues (FR); Olivier Bonzom, Nimes (FR); Sebastien Fort, Vaulnaveys-le-Haut (FR); Sylvie Armand, Grenoble (FR); Stephanie Pradeau, Saint-Honore (FR); Antoine Margeot, Paris (FR); Lionel Rousseau, Issou (FR); Françoise Le Roux, Rueil Malmaison (FR)

(73) Assignees: IFP Energies Nouvelles, Rueil Malmaison (FR); Centre National De La Recherche Scientifique—CNRS, Paris (FR); Proteus, Longjumeau (FR)

( * ) Notice: Subject to any disclaimer, the term of this patent is extended or adjusted under 35 U.S.C. 154(b) by 0 days.

(21) Appl. No.: 15/320,425

(22) PCT Filed: Jun. 12, 2015

(86) PCT No.: PCT/FR2015/051556
§ 371 (c)(1),
(2) Date: Dec. 20, 2016

(87) PCT Pub. No.: WO2015/193587
PCT Pub. Date: Dec. 23, 2015

(65) Prior Publication Data
US 2017/0152497 A1    Jun. 1, 2017

(30) Foreign Application Priority Data
Jun. 20, 2014  (FR) ..................... 14 55700

(51) Int. Cl.
| C12N 9/24 | (2006.01) |
| C12P 7/02 | (2006.01) |
| C12P 7/10 | (2006.01) |
| C12P 7/16 | (2006.01) |
| C12P 7/18 | (2006.01) |
| C12N 9/42 | (2006.01) |

(52) U.S. Cl.
CPC ......... *C12N 9/2437* (2013.01); *C12N 9/2405* (2013.01); *C12P 7/10* (2013.01); *C12Y 302/01091* (2013.01); *Y02E 50/16* (2013.01)

(58) Field of Classification Search
None
See application file for complete search history.

(56) References Cited

U.S. PATENT DOCUMENTS

2009/0162916 A1* 6/2009 Adney ........... C12Y 302/01091
435/209

FOREIGN PATENT DOCUMENTS

| WO | WO-2004016760 A2 * | 2/2004 | ......... C11D 3/38645 |
| WO | WO-2014093294 A1 * | 6/2014 | .............. C12P 19/14 |

OTHER PUBLICATIONS

UniProt Database Accession No. P62694, Feb. 2014, 4 pages (Year: 2014).*
The International Search Report (ISR) for PCT/FR2015/051556 dated Aug. 26, 2015, pp. 1-4.
Database Gene seq [Online]Jun. 19, 2014 (Jun. 19, 2014), "Hypocrea jecorina CBH1 polypeptide, SEQ ID 2." XP002732689, retrieved from EBI accession No. GSP:BBI75603 Database accession No. BBI75603.
Database Geneseq [Online] Jun. 19, 2014 (Jun. 19, 2014), "Hypocrea jecorina cellobiohydrolase 1 (CBH1) protein, SEQ ID 2.", XP002732690, retrieved from EBI accession No. GSP:BBI74548 Database accession No. BBI74548.
Database Geneseq [Online] Mar. 13, 2014 (Mar. 13, 2014), "Trichoderma reesei cellobiohydrolase I ' SEQ ID 34.", XP002732691, retrieved from EBI accession No. GSP:BBB73564 Database accession No. BBB73564.
Database Geneseq [Online] Jul. 18, 2013 (Jul. 18, 2013), "T. reesei mutant CellA protein, Y371C.", XP002732692, retrieved from EBI accession No. GSP:BA094743 Database accession No. BA094743.
Database Geneseq [Online] Feb. 19, 2009 (Feb. 19, 2009), "Trichoderma reesei cellobiohydrolase I protein, SEQ: 88.", XP002732693, retrieved from EBI accession No. GSP:AUP68912 Database accession No. AUP68912.

* cited by examiner

*Primary Examiner* — David Steadman
(74) *Attorney, Agent, or Firm* — McDonnell Boehnen Hulbert & Berghoff LLP

(57) ABSTRACT

The present invention relates to the expression and optimization of enzymes involved in the breakdown of lignocellulosic biomass. Disclosed are variants of the exoglucanase 1 of *Trichoderma reesei*, as well as the use of said variants with improved efficiency in methods for breaking down cellulose and for producing biofuel.

11 Claims, 5 Drawing Sheets
Specification includes a Sequence Listing.

SEQUENCE LISTING

<160> NUMBER OF SEQ ID NOS: 26

<210> SEQ ID NO 1
<211> LENGTH: 1545
<212> TYPE: DNA
<213> ORGANISM: Trichoderma reesei

<400> SEQUENCE: 1

```
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct gcgcgaagaa ctgctgtctg acggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctctacttcg tgtccatgga cgcggatggt ggcgtgagca agtatcccac caacaccgct     540
ggcgccaagt acggcacggg gtactgtgac agccagtgtc ccgcgatct gaagttcatc     600
aatggccagg ccaacgttga gggctgggag ccgtcatcca caacgcgaa cacgggcatt     660
ggaggacacg gaagctgctg ctctgagatg gatatctggg aggccaactc catctccgag     720
gctcttaccc ccaccccttg cacgactgtc ggccaggaga tctgcgaggg tgatgggtgc     780
ggcggaactt actccgataa cagatatggc ggcacttgcg atcccgatgg ctgcgactgg     840
aacccatacc gcctgggcaa caccagcttc tacggccctg gctcaagctt taccctcgat     900
accaccaaga aattgaccgt tgtcacccag ttcgagacgt cgggtgccat caaccgatac     960
tatgtccaga tggcgtcac tttccagcag cccaacgccg agcttggtag ttactctggc    1020
aacgagctca cgatgatta ctgcacagct gaggaggcag aattcggcgg atcctctttc    1080
tcagacaagg gcggcctgac tcagttcaag aaggctacct ctggcggcat ggttctggtc    1140
atgagtctgt gggatgatta ctacgccaac atgctgtggc tggactccac ctacccgaca    1200
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccaccgccg cccagccact accactggaa gctctcccgg acctacccag    1440
tctcactacg ccagtgcgg cggtattggc tacagcggcc ccacggtctg cgccagcggc    1500
acaacttgcc aggtcctgaa cccttactac tctcagtgcc tgtaa                    1545
```

<210> SEQ ID NO 2
<211> LENGTH: 514
<212> TYPE: PRT
<213> ORGANISM: Trichoderma reesei

<400> SEQUENCE: 2

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
            35                  40                  45
```

-continued

```
Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Gly Thr Thr Thr
    450                 455                 460

Thr Arg Arg Pro Ala Thr Thr Thr Gly Ser Ser Pro Gly Pro Thr Gln
```

Ser His Tyr Gly Gln Cys Gly Gly Ile Gly Tyr Ser Gly Pro Thr Val
465                 470                 475                 480
                485                         490                         495

Cys Ala Ser Gly Thr Thr Cys Gln Val Leu Asn Pro Tyr Tyr Ser Gln
                500                         505                         510

Cys Leu

<210> SEQ ID NO 3
<211> LENGTH: 1542
<212> TYPE: DNA
<213> ORGANISM: Artificial Sequence
<220> FEATURE:
<223> OTHER INFORMATION: Clone 32F9

<400> SEQUENCE: 3

```
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca ctggcgctg gactcacgct     180
acgaacagca gcacgaactg ctacgatggc aacacttgga gctcgaccct atgtcctgac     240
aacgagacct gcgcgaagaa ctgctgtctg acggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctttacttcg tgtccatgga cgcggatggt ggcgtgagca agtatcccac caacaccgct     540
ggcgccaagt acggcacggg gtactgtgac agccagtgtc ccgcgatct gaagttcatc     600
aatggccagg ccaacgttga gggctgggag ccgtcatcca caacgcgaa cacgggcatt     660
ggaggacacg gaagctgctg ctctgagatg gatatctggg aggccaactc catctccgag     720
gctcttaccc ccaccccttg cacgactgtc ggccaggaga tctgcgaggg tgatgggtgc     780
ggcggaactt actccgataa cagatatggc ggcacttgcg atcccgatgg ctgcgactgg     840
aacccatacc gcctgggcaa caccagcttc tacggccctg gctcaagctt taccctcgat     900
accaccaaga aattgaccgt tgtcacccag ttcgagacgt cgggtgccat caaccgatac     960
tatgtccaga tggcgtcac tttccagcag cccaacgccg agcttggtag ttactctggc    1020
aacgagctca cgatgatta ctgcacagct gaggaggcag aattcggcgg atcctctttc    1080
tcagacaagg gcggcctgac tcagttcaag aaggctacct ctggcggcat ggttctggtc    1140
atgagtctgt gggatgatta ctccgtcaac atgctgtggc tggactccac ctacccgaca    1200
aacgccaccg gtacacccgg tgccgctcgc ggaacctgct ccaccagctc cggttcacct    1260
aagaccgtcg aagccaactc tcccaacgcc aaggtcacct tctccaacat caagttcgga    1320
cccattggca gcaccggcaa ccctagcggc ggcaaccctc ccggcggaaa cccgcctggc    1380
accaccacca cccgccgccc agccactacc actggaagct ctcccggacc tacccagtct    1440
cactacggcc agtgcggcgg tattggctac agcggcccca cggtctgcgc cagcggcaca    1500
acttgccagg tcctgaaccc ttactactct cagtgcctgt aa                       1542
```

<210> SEQ ID NO 4
<211> LENGTH: 513
<212> TYPE: PRT
<213> ORGANISM: Artificial Sequence
<220> FEATURE:
<223> OTHER INFORMATION: Clone 32F9

```
<400> SEQUENCE: 4

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Ser Val Asn Met Leu Trp Leu Asp Ser Thr Tyr Pro Thr
385                 390                 395                 400

Asn Ala Thr Gly Thr Pro Gly Ala Ala Arg Gly Thr Cys Ser Thr Ser
```

```
                  405                 410                 415
Ser Gly Ser Pro Lys Thr Val Glu Ala Asn Ser Pro Asn Ala Lys Val
                420                 425                 430

Thr Phe Ser Asn Ile Lys Phe Gly Pro Ile Gly Ser Thr Gly Asn Pro
                435                 440                 445

Ser Gly Gly Asn Pro Pro Gly Gly Asn Pro Pro Gly Thr Thr Thr Thr
    450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
                500                 505                 510

Leu

<210> SEQ ID NO 5
<211> LENGTH: 1545
<212> TYPE: DNA
<213> ORGANISM: Artificial Sequence
<220> FEATURE:
<223> OTHER INFORMATION: Clone 64C2

<400> SEQUENCE: 5
atgtatcgga agttggccgt catctcggcc ttcttggcca cagctcgtgc tcagcaggtc      60
ggtacttccc aagcggaggt gcaccccgtcc atgacatggc agagctgcac tgctggtggc    120
agctgcacta ccaacaacgg caaggtggtc atcgacgcca ctggcgctg gtgcacaaa      180 gtaggcgact acacgaactg ctacaccggc aacacttggg acaagaccct atgtcctgac    240
gatgcaacct cgcgtccaa ctgcgccctg gagggtgcca actaccagtc cacgtacgga     300
gcgaccacga gcggtgacag cctccgcctc aactttgtca ccacctctca gcagaagaac    360
gttggcgctc gccttacct tatggcgagc gacacgacct accaggaatt caccctgctt    420
ggcaacgagt tctcttcga tgttgatgtt cgcagctgc cgtgcggctt gaacggagct     480 cttacttcg tgtccatgga cgcggatggt ggcgtgagca agtatcccac caacaccgct    540
ggcgccaagt acggcacggg gtactgtgac agccagtgtc cccgcgatct gaagttcatc    600
aatggccagg ccaacgttga gggctgggag ccgtcatcca caacgcgaa cacgggcatt     660 ggaggacacg gaagctgctg ctctgagatg gatatctggg aggccaactc catctccgag    720
gctcttaccc ccaccccttg cacgactgtc ggccaggaga tctgcgaggg tgatgggtgc    780
ggcggaactt actccgataa cagatatggc ggcacttgcg atcccgatgg ctgcgactgg    840
aacccatacc gcctgggcaa caccagcttc tacggccctg gctcaagctt acccctcgat    900
accaccaaga aattgaccgt tgtcacccag ttcgagacgt cgggtgccat caaccgatac    960
tatgtccaga tggcgtcac tttccagcag cccaacgccg agcttggtag ttactctggc   1020
aacgagctca cgatgatta ctgcacagct gaggaggcag aattcggcgg atcctctttc    1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
aacgagacct cctccacacc cggtgccgtg cgcggaagct gctccaccag ctccggtgtc   1260
cctgctcagg tcgaatctca gtctcccaac gccaaggtca ccttctccaa catcaagttc   1320
ggacccattg gcagcaccgg caaccctagc ggcggcaacc ctcccggcgg aaacccgcct   1380
ggcaccacca ccaccccgcc cccagccact accactggaa gctctcccgg acctacccag   1440
```

```
tctcactacg gccagtgcgg cggtattggc tacagcggcc ccacggtctg cgccagcggc      1500
acaacttgcc aggtcctgaa cccttactac tctcagtgcc tgtaa                     1545
```

<210> SEQ ID NO 6
<211> LENGTH: 514
<212> TYPE: PRT
<213> ORGANISM: Artificial Sequence
<220> FEATURE:
<223> OTHER INFORMATION: Clone 64C2

<400> SEQUENCE: 6

```
Met Tyr Arg Lys Leu Ala Val Ile Ser Ala Phe Leu Ala Thr Ala Arg
1               5                   10                  15

Ala Gln Gln Val Gly Thr Ser Gln Ala Glu Val His Pro Ser Met Thr
                20                  25                  30

Trp Gln Ser Cys Thr Ala Gly Gly Ser Cys Thr Thr Asn Asn Gly Lys
            35                  40                  45

Val Val Ile Asp Ala Asn Trp Arg Trp Val His Lys Val Gly Asp Tyr
        50                  55                  60

Thr Asn Cys Tyr Thr Gly Asn Thr Trp Asp Lys Thr Leu Cys Pro Asp
65                  70                  75                  80

Asp Ala Thr Cys Ala Ser Asn Cys Ala Leu Glu Gly Ala Asn Tyr Gln
                85                  90                  95

Ser Thr Tyr Gly Ala Thr Thr Ser Gly Asp Ser Leu Arg Leu Asn Phe
                100                 105                 110

Val Thr Thr Ser Gln Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
        130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
        210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
        290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
```

```
                    340             345             350
Ala Glu Phe Gly Gly Ser Ser Phe Ser Asp Lys Gly Gly Leu Thr Gln
                355                     360                 365

Phe Lys Lys Ala Thr Ser Gly Gly Met Val Leu Val Met Ser Leu Trp
        370                     375                 380

Asp Asp Tyr Tyr Ala Asn Met Leu Trp Leu Asp Ser Thr Tyr Pro Thr
385                     390                     395                 400

Asn Glu Thr Ser Ser Thr Pro Gly Ala Val Arg Gly Ser Cys Ser Thr
                    405                     410                 415

Ser Ser Gly Val Pro Ala Gln Val Glu Ser Gln Ser Pro Asn Ala Lys
                420                     425                 430

Val Thr Phe Ser Asn Ile Lys Phe Gly Pro Ile Gly Ser Thr Gly Asn
            435                     440                 445

Pro Ser Gly Gly Asn Pro Pro Gly Gly Asn Pro Pro Gly Thr Thr Thr
        450                     455                 460

Thr Arg Arg Pro Ala Thr Thr Thr Gly Ser Ser Pro Gly Pro Thr Gln
465                     470                     475                 480

Ser His Tyr Gly Gln Cys Gly Gly Ile Gly Tyr Ser Gly Pro Thr Val
                    485                     490                 495

Cys Ala Ser Gly Thr Thr Cys Gln Val Leu Asn Pro Tyr Tyr Ser Gln
                500                     505                 510

Cys Leu

<210> SEQ ID NO 7
<211> LENGTH: 1545
<212> TYPE: DNA
<213> ORGANISM: Artificial Sequence
<220> FEATURE:
<223> OTHER INFORMATION: Clone 130G9

<400> SEQUENCE: 7
atgtatcgga agttggccgt catctcggcc ttcttggcca cagctcgtgc tcagtcggcc        60
tgcactctcc aatcggagac tcacccgcct ctgacatggc agaaatgctc gtctggtggc       120
acgtgcactc aacagacagg ctccgtggtc atcgacgcca ctggcgctg gactcacgct        180 acgaacagca gcacgaactg ctacgatggc aacacttgga gctcgaccct atgtcctgac       240
aacgagacct cgcgcaagaa ctgctgtctg gacggtgccg cctacgcgtc cacgtacgga       300
gttaccacga gcggtaacag cctctccatt ggctttgtca cccagtctgc gcagaagaac       360
gttggcgctc gccttacct tatggcgagc gacacgacct accaggaatt caccctgctt       420
ggcaacgagt tctctttcga tgttgatgtt tcgcagctgc cgtgcggctt gaacggagct       480
ctttacttcg tgtccatgga cgcggatggt ggcgtgagca agtatcccac caacaccgct       540
ggcgccaagt acggcacggg gtactgtgac agccagtgtc cccgcgatct gaagttcatc       600
aatggccagg ccaacgttga gggctggcag ccgtcatcca caacgcgaa cacgggcatt       660 ggaggacacg gaagctgctg ctctgagatg gatatctggg aggccaactc catctccgag       720
gctcttaccc ccacccttg cgacactccc ggccaggtga tctgcgaggg tgatgggtgc       780
ggcggaactt actccgataa cagatatggc ggcacttgcg atcccgatgg ctgcgactgg       840
aacccatacc gcctgggcaa caccagcttc tacggccctg ctcaagcttt accctcgat       900 accaccaaga aattgaccgt tgtcacccag ttcgagacgt cgggtgccat caaccgatac       960
tatgtccaga atggcgtcac tttccagcag cccaacgccg agcttggtag ttactctggc      1020
aacgagctca acgatgatta ctgcacagct gaggaggcag aattcggcgg atcctctttc      1080
```

```
tcagacaagg gcggcctgac tcagttcaag aaggctacct ctggcggcat ggttctggtc    1140
atgagtctgt gggatgatta ctacgccaac atgctgtggc tggactccac ctacccgaca    1200
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccaccgccg cccagccact accactggaa gctctcccgg acctacccag    1440
tctcactacg gccagtgcgg cggtattggc tacagcggcc ccacggtctg cgccagcggc    1500
acaacttgcc aggtcctgaa cccttactac tctcagtgcc tgtaa                   1545
```

<210> SEQ ID NO 8
<211> LENGTH: 514
<212> TYPE: PRT
<213> ORGANISM: Artificial Sequence
<220> FEATURE:
<223> OTHER INFORMATION: Clone 130G9

<400> SEQUENCE: 8

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Asp Thr Pro Gly Gln Val Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
```

```
            275                 280                 285
Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 9
<211> LENGTH: 1542
<212> TYPE: DNA
<213> ORGANISM: Artificial Sequence
<220> FEATURE:
<223> OTHER INFORMATION: Clone 224C11

<400> SEQUENCE: 9
atgtatcgga agttggccgt catctcggcc ttcttggcca cagctcgtgc tcagtcggcc    60
tgcactctcc aatcggagac tcacccgcct ctgacatggc agaaatgctc gtctggtggc   120
acgtgcactc aacagacagg ctccgtggtc atcgacgcca ctggcgctg gactcacgct    180 acgaacagca gcacgaactg ctacgatggc aacacttgga gctcgaccct atgtcctgac   240
aacgagacct gcgcgaagaa ctgctgtctg acggtgccg cctacgcgtc cacgtacgga    300
gttaccacga gcggtaacag cctctccatt ggctttgtca cccagtctgc gcagaagaac   360
gttggcgctc gcctttacct tatggcgagc gacacgacct accaggaatt caccctgctt   420
ggcaacgagt tctcttttcga tgttgatgtt tcgcagctgc cgtgcggctt gaacggagct   480 cttactcg tgtccatgga cgcggatggt ggcgtgagca agtatccacc aacaccgct    540 ggcgccaagt acggcacggg gtactgtgac agccagtgtc ccgcgatct gaagttcatc    600 aatggccagc caacgttga gggctgggag ccgtcatcca acaacgcgaa cacgggcatt   660
ggaggacacg gaagctgctg ctctgagatg gatatctggg aggccaactc catctccgag   720
```

```
gctcttaccc cccacccttg cacgactgtc ggccaggaga tctgcgaggg tgatgggtgc    780
ggcggaactt actccgataa cagatatggc ggcacttgcg atcccgatgg ctgcgactgg    840
aacccatacc gcctgggcaa caccagcttc tacggccctg gctcaagctt taccctcgat    900
accaccaaga aattgaccgt tgtcacccag ttcgagacgt cgggtgccat caaccgatac    960
tatgtccaga tggcgtcac tttccagcag cccaacgccg agcttggtag ttactctggc   1020
aacgagctca cgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctaccccaca   1200
aacgccaccg gtacacccgg tgccgtgcgc ggaagctgct ccaccagctc cggtgtccct   1260
gctcaggtcg aatctcagtc tcccaacgcc aaggtcacct tctccaacat caagttcgga   1320
cccattggca gcaccggcaa ccctagcggc ggcaacccctc ccggcggaaa cccgcctggc   1380
accaccacca cccgccgccc agccactacc actggaagct ctcccggacc tacccagtct   1440
cactacggcc agtgcggcgg tattggctac agcggcccca cggtctgcgc cagcggcaca   1500
acttgccagg tcctgaaccc ttactactct cagtgcctgt aa                      1542
```

<210> SEQ ID NO 10
<211> LENGTH: 513
<212> TYPE: PRT
<213> ORGANISM: Artificial Sequence
<220> FEATURE:
<223> OTHER INFORMATION: Clone 224C11

<400> SEQUENCE: 10

```
Met Tyr Arg Lys Leu Ala Val Ile Ser Ala Phe Leu Ala Thr Ala Arg
1               5                  10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
```

```
        210                 215                 220
Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Ala Thr Gly Thr Pro Gly Ala Val Arg Gly Ser Cys Ser Thr Ser
                405                 410                 415

Ser Gly Val Pro Ala Gln Val Glu Ser Gln Ser Pro Asn Ala Lys Val
                420                 425                 430

Thr Phe Ser Asn Ile Lys Phe Gly Pro Ile Gly Ser Thr Gly Asn Pro
            435                 440                 445

Ser Gly Gly Asn Pro Pro Gly Gly Asn Pro Pro Gly Thr Thr Thr Thr
    450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
            500                 505                 510

Leu
```

<210> SEQ ID NO 11
<211> LENGTH: 1542
<212> TYPE: DNA
<213> ORGANISM: Artificial Sequence
<220> FEATURE:
<223> OTHER INFORMATION: Clone 225B11

<400> SEQUENCE: 11

```
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct gcgcgaagaa ctgctgtctg acggtgccg cctacgcgtc cacgtacgga     300
gttaccacga gcggtaacag cctctccatt ggctttgtca cccagtctgc gcagaagaac     360
```

```
gttggcgctc gcctttacct tatggcgagc gacacgacct accaggaatt caccctgctt    420
ggcaacgagt tctctttcga tgttgatgtt tcgcagctgc cgtgcggctt gaacggagct    480
ctttacttcg tgtccatgga cgcggatggt ggcgtgagca agtatcccac caacaccgct    540
ggcgccaagt acggcacggg gtactgtgac agccagtgtc cccgcgatct gaagttcatc    600
aatggccagg ccaacgttga gggctgggag ccgtcatcca caacgcgaa cgggcatt       660
ggaggacacg gaagctgctg ctctgagatg gatatctggg aggccaactc catctccgag    720
gctcttaccc ccacccttg cacgactgtc ggccaggaga tctgcgaggg tgatgggtgc     780
ggcggaactt actccgataa cagatatggc ggcacttgcg atcccgatgg ctgcgactgg    840
aacccatacc gcctgggcaa caccagcttc tacggccctg gctcaagctt accctcgat    900
accaccaaga aattgaccgt tgtcacccag ttcgagacgt cgggtgccat caaccgatac    960
tatgtccaga atggcgtcac tttccagcag cccaacgccg agcttggtag ttactctggc   1020
aacgagctca cgatgatta ctgcacagct gaggaggcag aattcggcgg atcctctttc     1080
tcagacaagg gcggcctgac tcagttcaag aaggctacct ctggcggcat ggttctggtc   1140
atgagtctgt gggatgatta ctccgtcaac atgctgtggc tggactccac ctacccgaca   1200
aacgccaccg gtacacccgg tgccgctcgc ggaacctgct ccaccagctc cggtgtccct   1260
gctcaggtcg aatctcagtc tcccaacgcc aaggtcacct tctccaacat caagttcgga   1320
cccattggca gcaccggcaa ccctagcggc ggcaacccct ccggcggaaa cccgcctggc   1380
accaccacca cccgccgccc agccactacc actggaagct ctcccggacc tacccagtct   1440
cactacggcc agtgcggcgg tattggctac agcggcccca cggtctgcgc cagcggcaca   1500
acttgccagg tcctgaaccc ttactactct cagtgcctgt aa                       1542

<210> SEQ ID NO 12
<211> LENGTH: 505
<212> TYPE: PRT
<213> ORGANISM: Artificial Sequence
<220> FEATURE:
<223> OTHER INFORMATION: Clone 225B11

<400> SEQUENCE: 12

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
```

```
            145                 150                 155                 160
Leu Tyr Phe Val Ser Met Asp Ala Asp Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
        210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Ser Val Asn Met Leu Trp Leu Asp Ser Thr Tyr Pro Thr
385                 390                 395                 400

Asn Ala Thr Gly Thr Pro Gly Ala Ala Arg Gly Thr Cys Ser Thr Ser
                405                 410                 415

Ser Gly Val Pro Ala Gln Val Glu Ser Gln Ser Pro Asn Ala Lys Val
            420                 425                 430

Thr Phe Ser Asn Ile Lys Phe Gly Pro Ile Gly Ser Thr Gly Asn Pro
        435                 440                 445

Ser Gly Gly Asn Pro Pro Gly Gly Asn Pro Pro Gly Thr Thr Thr Thr
    450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu
            500                 505

<210> SEQ ID NO 13
<211> LENGTH: 1545
<212> TYPE: DNA
<213> ORGANISM: Artificial Sequence
<220> FEATURE:
<223> OTHER INFORMATION: Clone 242D11

<400> SEQUENCE: 13
atgtatcgga agttggccgt catctcggcc ttcttggcca cagctcgtgc tcagtcggcc    60
```

-continued

```
tgcactctcc aatcggagac tcacccgcct ctgacatggc agaaatgctc gtctggtggc      120
acgtgcactc aacagacagg ctccgtggtc atcgacgcca actggcgctg gactcacgct      180
acgaacagca gcacgaactg ctacgatggc aacacttgga gctcgaccct atgtcctgac      240
aacgagacct cgcgcaagaa ctgctgtctg acggtgccg cctacgcgtc cacgtacgga       300
gttaccacga gcggtaacag cctctccatt ggctttgtca cccagtctgc gcagaagaac      360
gttggcgctc gcctttacct tatggcgagc gacacgacct accaggaatt caccctgctt      420
ggcaacgagt tctctttcga tgttgatgtt tcgcagctgc cgtgcggctt gaacggagct      480
ctttacttcg tgtccatgga cgcggatggt ggcgtgagca agtatcccac caacaccgct      540
ggcgccaagt acggcacggg gtactgtgac agccagtgtc ccgcgatct gaagttcatc       600 aatggccagg ccaacgttga gggctggcag ccgtcatcca cgatgcgaa cgcgggcacc       660 ggaaaccacg gaagctgctg ctctgagatg gatatctggg aggccaactc catctccgag      720
gctcttaccc cccacccttg cacgactgtc ggccaggaga tctgcgaggg tgatgggtgc      780
ggcggaactt actccgataa cagatatggc ggcacttgcg atcccgatgg ctgcgactgg      840
aacccatacc gcctgggcaa caccagcttc tacggccctg gctcaagctt accctcgat       900 accaccaaga aattgaccgt tgtcacccag ttcgagacgt cgggtgccat caaccgatac      960
tatgtccaga atggcgtcac tttccagcag cccaacgccg agcttggtag ttactctggc     1020
aacgagctca cgatgatta ctgcacagct gaggaggcag aattcggcgg atcctctttc      1080
tcagacaagg gcggcctgac tcagttcaag aaggctacct ctggcggcat ggttctggtc     1140
atgagtctgt gggatgatta ctacgccaac atgctgtggc tggactccac ctacccgaca     1200
aacgagacct cctccacacc cggtgccgtg cgcggaagct gctccaccag ctccggtgtc     1260
cctgctcagg tcgaatctca gtctcccaac gccaaggtca ccttctccaa catcaagttc     1320
ggacccattg gcagcaccgg caaccctagc ggcggcaacc ctcccggcgg aaacccgcct     1380
ggcaccacca ccacccgccg cccagccact accactggaa gctctcccgg acctacccag     1440
tctcactacg gccagtgcgg cggtattggc tacagcggcc ccacggtctg cgccagcggc     1500
acaacttgcc aggtcctgaa cccttactac tctcagtgcc tgtaa                     1545
```

<210> SEQ ID NO 14
<211> LENGTH: 514
<212> TYPE: PRT
<213> ORGANISM: Artificial Sequence
<220> FEATURE:
<223> OTHER INFORMATION: Clone 242D11

<400> SEQUENCE: 14

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95
```

```
Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ser Asn Asp Ala Asn Ala Gly Thr Gly Asn His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu
```

<210> SEQ ID NO 15
<211> LENGTH: 1545
<212> TYPE: DNA
<213> ORGANISM: Artificial Sequence
<220> FEATURE:
<223> OTHER INFORMATION: Clone 453E8

<400> SEQUENCE: 15

```
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct cgcgcaagaa ctgctgtctg acggtgccga ctactcgggg aacgtacgga     300
attaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctttacttcg tgtccatgga cgcggatggt ggcgtgagca agtatcccac caacaccgct     540
ggcgccaagt acggcacggg gtactgtgac agccagtgtc ccgcgatct gaagttcatc      600
aatggccagg ccaacgttga gggctgggag ccgtcatcca caacgcgaa cacgggcatt      660
ggaggacacg gaagctgctg ctctgagatg gatatctggg aggccaactc catctccgag     720
gctcttaccc ccaccccttg cacgactgtc ggccaggaga tctgcgaggg tgatgggtgc     780
ggcggaactt actccgataa cagatatggc ggcacttgcg atcccgatgg ctgcgactgg     840
aacccatacc gcctgggcaa caccagcttc tacggccctg gctcaagctt taccctcgat     900
accaccaaga aattgaccgt tgtcacccag ttcgagacgt cgggtgccat caaccgatac     960
tatgtccaga tggcgtcac tttccagcag cccaacgccg agcttggtag ttactctggc    1020
aacgagctca cgatgatta ctgcacagct gaggaggcag aattcggcgg atcctctttc     1080
tcagacaagg gcggcctgac tcagttcaag aaggctacct ctggcggcat ggttctggtc    1140
atgagtctgt gggatgatta ctacgccaac atgctgtggc tggactccac ctacccgaca    1200
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccacccgccg cccagccact accactggaa gctctcccgg acctacccag    1440
tctcactacg ccagtgcgg cggtattggc tacagcggcc ccacggtctg cgccagcggc    1500
acaacttgcc aggtcctgaa cccttactac tctcagtgcc tgtaa                     1545
```

<210> SEQ ID NO 16
<211> LENGTH: 514
<212> TYPE: PRT
<213> ORGANISM: Artificial Sequence
<220> FEATURE:
<223> OTHER INFORMATION: Clone 453E8

<400> SEQUENCE: 16

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30
```

-continued

```
Trp Gln Lys Cys Ser Ser Gly Thr Cys Thr Gln Thr Gly Ser
         35                  40              45

Val Val Ile Asp Ala Asn Trp Arg Trp Thr His Ala Thr Asn Ser Ser
 50                  55                  60

Thr Asn Cys Tyr Asp Gly Asn Thr Trp Ser Ser Thr Leu Cys Pro Asp
 65              70                  75                      80

Asn Glu Thr Cys Ala Lys Asn Cys Cys Leu Asp Gly Ala Asp Tyr Ser
                 85                  90                  95

Gly Thr Tyr Gly Ile Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
```

```
                450            455            460
Thr Arg Arg Pro Ala Thr Thr Thr Gly Ser Ser Pro Gly Pro Thr Gln
465                 470                475                480

Ser His Tyr Gly Gln Cys Gly Gly Ile Gly Tyr Ser Gly Pro Thr Val
                485                490                495

Cys Ala Ser Gly Thr Thr Cys Gln Val Leu Asn Pro Tyr Tyr Ser Gln
            500                505                510

Cys Leu

<210> SEQ ID NO 17
<211> LENGTH: 1542
<212> TYPE: DNA
<213> ORGANISM: Artificial Sequence
<220> FEATURE:
<223> OTHER INFORMATION: Clone B

<400> SEQUENCE: 17
atgtatcgga agttggccgt catctcggcc ttcttggcca cagctcgtgc tcagtcggcc        60
tgcactctcc aatcggagac tcacccgcct ctgacatggc agaaatgctc gtctggtggc      120
acgtgcactc aacagacagg ctccgtggtc atcgacgcca actggcgctg gactcacgct      180
acgaacagca gcacgaactg ctacgatggc aacacttgga gctcgaccct atgtcctgac      240
aacgagacct cgcgaagaa ctgctgtctg acggtgccg actactcggg aacgtacgga        300
attaccacga gcggtaacag cctctccatt ggctttgtca cccagtctgc gcagaagaac      360
gttggcgctc gcctttacct tatggcgagc gacacgacct accaggaatt caccctgctt      420
ggcaacgagt tctcttttcga tgttgatgtt tcgcagctgc cgtgcggctt gaacggagct      480
ctttacttcg tgtccatgga cgcggatggt ggcgtgagca agtatcccac caacaccgct      540
ggcgccaagt acggcacggg gtactgtgac agccagtgtc ccgcgatct gaagttcatc       600 aatggccagg ccaacgttga gggctgggag ccgtcatcca caacgcgaa cacgggcatt       660 ggaggacacg gaagctgctg ctctgagatg gatatctggg aggccaactc catctccgag     720
gctcttaccc cccaccttg cgacactccc ggccaggtga tctgcgaggg tgatgggtgc      780
ggcggaactt actccgataa cagatatggc ggcacttgcg atcccgatgg ctgcgactgg     840
aacccatacc gcctgggcaa caccagcttc tacggccctg gctcaagctt taccctcgat     900
accaccaaga aattgaccgt tgtcacccag ttcgagacgt cgggtgccat caaccgatac     960
tatgtccaga tggcgtcac tttccagcag cccaacgccg agcttggtag ttactctggc     1020
aacgagctca cgatgatta ctgcacagct gaggaggcag aattcggcgg atcctctttc     1080
tcagacaagg gcggcctgac tcagttcaag aaggctacct ctggcggcat ggttctggtc    1140
atgagtctgt gggatgatta ctccgtcaac atgctgtggc tggactccac ctacccgaca    1200
aacgccaccg gtacacccgg tgccgctcgc ggaacctgct ccaccagctc cggttcacct    1260
aagaccgtcg aagccaactc tcccaacgcc aaggtcacct tctccaacat caagttcgga  1320
cccattggca gcaccggcaa ccctagcggc ggcaacccctc ccggcggaaa cccgcctggc   1380
accaccacca cccgccgccc agccactacc actggaagct ctcccggacc tacccagtct    1440
cactacggcc agtgcggcgg tattggctac agcggcccca cggtctgcgc cagcggcaca    1500
acttgccagg tcctgaaccc ttactactct cagtgcctgt aa                       1542

<210> SEQ ID NO 18
<211> LENGTH: 513
<212> TYPE: PRT
```

<213> ORGANISM: Artificial Sequence
<220> FEATURE:
<223> OTHER INFORMATION: Clone B

<400> SEQUENCE: 18

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65              70                  75                  80

Asn Glu Thr Cys Ala Lys Asn Cys Cys Leu Asp Gly Ala Asp Tyr Ser
                85                  90                  95

Gly Thr Tyr Gly Ile Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Asp Thr Pro Gly Gln Val Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Ser Val Asn Met Leu Trp Leu Asp Ser Thr Tyr Pro Thr
```

```
            385                 390                 395                 400
Asn Ala Thr Gly Thr Pro Gly Ala Ala Arg Gly Thr Cys Ser Thr Ser
                405                 410                 415
Ser Gly Ser Pro Lys Thr Val Glu Ala Asn Ser Pro Asn Ala Lys Val
                420                 425                 430
Thr Phe Ser Asn Ile Lys Phe Gly Pro Ile Gly Ser Thr Gly Asn Pro
                435                 440                 445
Ser Gly Gly Asn Pro Pro Gly Gly Asn Pro Pro Gly Thr Thr Thr Thr
                450                 455                 460
Arg Arg Pro Ala Thr Thr Thr Gly Ser Ser Pro Gly Pro Thr Gln Ser
465                 470                 475                 480
His Tyr Gly Gln Cys Gly Gly Ile Gly Tyr Ser Gly Pro Thr Val Cys
                485                 490                 495
Ala Ser Gly Thr Thr Cys Gln Val Leu Asn Pro Tyr Tyr Ser Gln Cys
                500                 505                 510
Leu

<210> SEQ ID NO 19
<211> LENGTH: 1545
<212> TYPE: DNA
<213> ORGANISM: Artificial Sequence
<220> FEATURE:
<223> OTHER INFORMATION: Clone 91D9

<400> SEQUENCE: 19
atgtatcgga agttggccgt catctcggcc ttcttggcca cagctcgtgc tcagtcggcc      60
tgcactctcc aatcggggac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct gcgcgaagaa ctgctgtctg acggtgccg accgctcggg aacgtacgga     300
attaccacga gcggtaacag cctctccatt ggctttgtca cccagtctgc gcagaagaac     360
gttggcgctc gcctttacct tatggcgagc gacacgacct acctggaatt caccctgctt     420
ggcaacgagt tctctttcga tgttgatgtt tcgcagctgc cgtgcggctt gaacggagct     480 cttacttcg tgtccatgga cgcggatggt ggcgtgagca agtatccac caacaccgct     540 ggcgccaagt acggcacggg gtactgtgac agccagtgtc cccgcgatct gaagttcatc     600
aatggccagg ccaacgttga gggctggag ccgtcatcca caacgcgaa cacgggcatt     660 ggaggacgcg gaagctgctg ctctgagatg gatatctggg aggccaactc catctccgag     720
gctcttaccc ccaccccttg catgactgtc ggccaggaga tctgcgaggg tgatgggtgc     780
ggcggaactt actccgataa cagatatggc ggcacttgcg atcccgatgg ctgcgactgg     840
aacccatacc gcctgggcaa caccagcttc tacggccctg gctcaagctt accctcgat     900 accaccaaga aattgaccgt tgtcacccag ttcgagacgt cgggtgccat caaccgatac     960
tatgtccaga atggcgtcac tttccagcag cccaacgccg agcttggtag ttactctggc    1020
aacgagctcg acgatgatta ctgcacagct gaggaggcag aattcggcgg atcctctttc    1080
tcagacaagg gcggcctgac tcagttcaag aaggctacct ctggcggcat ggttctggtc    1140
atgagtctgt gggatgatta ctacgccaac atgctgtggc tggactccac ctacccgaca    1200
aacgagacct cctccacacc cggtgccgtg cgcggaagct gctccaccag ctccggtgtc    1260
cctgctcagg tcgaatctca gtctcccaac gccaaggtca ccttctccaa catcaagctc    1320
```

-continued

```
ggacccattg gcagcaccgg caaccctagc ggcggcaacc ctccggcgg aaacccgcct      1380 ggcaccacca ccaccgccg cccagccact accactggaa gctctcccgg acctaccag       1440 tctcactacg gccagtgcgg cggtattggc tacagcggcc ccacggtctg cgccagcggc     1500
acaacttgcc aggtcctgaa cccttactac tctcagtgcc tgtaa                    1545
```

<210> SEQ ID NO 20
<211> LENGTH: 514
<212> TYPE: PRT
<213> ORGANISM: Artificial Sequence
<220> FEATURE:
<223> OTHER INFORMATION: Clone 91D9

<400> SEQUENCE: 20

```
Met Tyr Arg Lys Leu Ala Val Ile Ser Ala Phe Leu Ala Thr Ala Arg
1               5                   10                  15

Ala Gln Ser Ala Cys Thr Leu Gln Ser Gly Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Asp Arg Ser
                85                  90                  95

Gly Thr Tyr Gly Ile Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Leu Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly Arg Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Met Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
```

|  |  |  | 325 |  |  |  | 330 |  |  |  | 335 |  |
|---|---|---|---|---|---|---|---|---|---|---|---|---|
| Ser | Tyr | Ser | Gly | Asn | Glu | Leu | Asp | Asp | Tyr | Cys | Thr | Ala | Glu | Glu |
|  |  |  | 340 |  |  |  | 345 |  |  |  | 350 |  |

| Ala | Glu | Phe | Gly | Gly | Ser | Ser | Phe | Ser | Asp | Lys | Gly | Gly | Leu | Thr | Gln |
|---|---|---|---|---|---|---|---|---|---|---|---|---|---|---|---|
|  |  |  | 355 |  |  |  | 360 |  |  |  | 365 |  |

| Phe | Lys | Lys | Ala | Thr | Ser | Gly | Gly | Met | Val | Leu | Val | Met | Ser | Leu | Trp |
|---|---|---|---|---|---|---|---|---|---|---|---|---|---|---|---|
| 370 |  |  |  |  | 375 |  |  |  |  | 380 |  |  |

| Asp | Asp | Tyr | Tyr | Ala | Asn | Met | Leu | Trp | Leu | Asp | Ser | Thr | Tyr | Pro | Thr |
|---|---|---|---|---|---|---|---|---|---|---|---|---|---|---|---|
| 385 |  |  |  |  | 390 |  |  |  |  | 395 |  |  |  |  | 400 |

| Asn | Glu | Thr | Ser | Ser | Thr | Pro | Gly | Ala | Val | Arg | Gly | Ser | Cys | Ser | Thr |
|---|---|---|---|---|---|---|---|---|---|---|---|---|---|---|---|
|  |  |  |  | 405 |  |  |  |  | 410 |  |  |  |  | 415 |  |

| Ser | Ser | Gly | Val | Pro | Ala | Gln | Val | Glu | Ser | Gln | Ser | Pro | Asn | Ala | Lys |
|---|---|---|---|---|---|---|---|---|---|---|---|---|---|---|---|
|  |  |  | 420 |  |  |  | 425 |  |  |  | 430 |  |  |

| Val | Thr | Phe | Ser | Asn | Ile | Lys | Leu | Gly | Pro | Ile | Gly | Ser | Thr | Gly | Asn |
|---|---|---|---|---|---|---|---|---|---|---|---|---|---|---|---|
|  |  |  | 435 |  |  |  | 440 |  |  |  | 445 |  |  |

| Pro | Ser | Gly | Gly | Asn | Pro | Pro | Gly | Gly | Asn | Pro | Pro | Gly | Thr | Thr | Thr |
|---|---|---|---|---|---|---|---|---|---|---|---|---|---|---|---|
|  | 450 |  |  |  |  | 455 |  |  |  |  | 460 |  |  |

| Thr | Arg | Arg | Pro | Ala | Thr | Thr | Thr | Gly | Ser | Ser | Pro | Gly | Pro | Thr | Gln |
|---|---|---|---|---|---|---|---|---|---|---|---|---|---|---|---|
| 465 |  |  |  |  | 470 |  |  |  |  | 475 |  |  |  |  | 480 |

| Ser | His | Tyr | Gly | Gln | Cys | Gly | Gly | Ile | Gly | Tyr | Ser | Gly | Pro | Thr | Val |
|---|---|---|---|---|---|---|---|---|---|---|---|---|---|---|---|
|  |  |  |  | 485 |  |  |  |  | 490 |  |  |  |  | 495 |  |

| Cys | Ala | Ser | Gly | Thr | Thr | Cys | Gln | Val | Leu | Asn | Pro | Tyr | Tyr | Ser | Gln |
|---|---|---|---|---|---|---|---|---|---|---|---|---|---|---|---|
|  |  |  | 500 |  |  |  |  | 505 |  |  |  |  | 510 |  |

Cys Leu

<210> SEQ ID NO 21
<211> LENGTH: 1566
<212> TYPE: DNA
<213> ORGANISM: Talaromyces stipitatus

<400> SEQUENCE: 21

```
atgtatcgga agttggccgt catctcggcc ttcttggcca cagctcgtgc tcagcaggtc      60
ggtacttccc aagcggaggt gcacccgtcc atgacatggc agagctgcac tgctggtggc     120
agctgcacta ccaacaacgg caaggtggtc atcgacgcca ctggcgctg gtgcacaaa      180
gtaggcgact acacgaactg ctacaccggc aacacttggg acaagaccct atgtcctgac     240
gatgcaacct gcgcgtccaa ctgcgccctg gagggtgcca actaccagtc cacgtacgga     300
gcgaccacga gcggtgacag cctccgcctc aactttgtca ccacctctca gcagaagaac     360
attggctcgc gcctttacat gatgaaggac gacacgacct acgagatgtt caagctgctt     420
aaccaggagt tcaccttcga tgttgatgtt tcgaacctgc cgtgcggctt gaacggagct     480
ctctacttcg tggccatgga cgcggatggt ggcatgagca gtatcccac caacaaggct     540
ggcgccaagt acggcacggg gtactgtgac agccagtgtc ccgcgatct gaagttcatc     600
aatggccagg ccaacgttga gggctggcag ccgtcatcca cgatgcgaa cgcgggcacc     660
ggaaaccacg gaagctgctg cgcggagatg gatatctggg aggccaactc catctccacg     720
gctttcaccc ccaccccttg cgacactccc ggccaggtga tgtgcaccgg tgatgcctgc     780
ggcggaactt actcctccga cagatatggc ggcacttgcg atcccgatgg ctgcgacttc     840
aactccttcc gccagggcaa caagaccttc tacggccctg gcatgaccgt cgataccaag     900
agcaaattca ccgttgtcac ccagttcatc acggacgatg gcaccgccag cggcacctc     960
aaggagatca agcgattcta tgtccagaat ggcaaggtga tccccaactc ggagtcgacc    1020
```

-continued

```
tggtccggcg tcggcggcaa ctccatcacc aacgattact gcacagctca gaagagcctg    1080
ttcaaggacc agaacgtctt cgccaagcac ggcggcatgg agggcatggg cgctgctctc    1140
gcccagggca tggttctggt catgagtctg tgggatgatc acgcggccaa catgctgtgg    1200
ctggactcca actacccgac aactgcctct cctccacac ccggtgtcgc ccgcggaacc     1260
tgcgacatca gctccggtgt ccctgctgat gtcgaagcta accacccga cgcctccgtc     1320 gtctactcca acatcaaggt cggacccatt ggcagcacct tcaacagcgg cggctcgaac    1380
cccggcggag gcaccaccac caccgcgaag ccaacgacga ccactaccac tgccggttct    1440
cccggaggca ccggagtcgc tcagcactac ggccagtgcg gcggtaatgg ctggcagggc    1500
cccacgacct gcgccagccc ttatacttgc cagaagctga cgacttttta ctctcagtgc    1560
ctgtaa                                                                1566
```

<210> SEQ ID NO 22
<211> LENGTH: 521
<212> TYPE: PRT
<213> ORGANISM: Talaromyces stipitatus

<400> SEQUENCE: 22

```
Met Tyr Arg Lys Leu Ala Val Ile Ser Ala Phe Leu Ala Thr Ala Arg
1               5                   10                  15

Ala Gln Gln Val Gly Thr Ser Gln Ala Glu Val His Pro Ser Met Thr
            20                  25                  30

Trp Gln Ser Cys Thr Ala Gly Gly Ser Cys Thr Thr Asn Asn Gly Lys
        35                  40                  45

Val Val Ile Asp Ala Asn Trp Arg Trp Val His Lys Val Gly Asp Tyr
    50                  55                  60

Thr Asn Cys Tyr Thr Gly Asn Thr Trp Asp Lys Thr Leu Cys Pro Asp
65                  70                  75                  80

Asp Ala Thr Cys Ala Ser Asn Cys Ala Leu Glu Gly Ala Asn Tyr Gln
                85                  90                  95

Ser Thr Tyr Gly Ala Thr Thr Ser Gly Asp Ser Leu Arg Leu Asn Phe
            100                 105                 110

Val Thr Thr Ser Gln Gln Lys Asn Ile Gly Ser Arg Leu Tyr Met Met
        115                 120                 125

Lys Asp Asp Thr Thr Tyr Glu Met Phe Lys Leu Leu Asn Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Met Ser Lys Tyr Pro
                165                 170                 175

Thr Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ser Asn Asp Ala Asn Ala Gly Thr Gly Asn His Gly
    210                 215                 220

Ser Cys Cys Ala Glu Met Asp Ile Trp Glu Ala Asn Ser Ile Ser Thr
225                 230                 235                 240

Ala Phe Thr Pro His Pro Cys Asp Thr Pro Gly Gln Val Met Cys Thr
                245                 250                 255

Gly Asp Ala Cys Gly Gly Thr Tyr Ser Ser Asp Arg Tyr Gly Gly Thr
            260                 265                 270
```

Cys Asp Pro Asp Gly Cys Asp Phe Asn Ser Phe Arg Gln Gly Asn Lys
            275                 280                 285

Thr Phe Tyr Gly Pro Gly Met Thr Val Asp Thr Lys Ser Lys Phe Thr
    290                 295                 300

Val Val Thr Gln Phe Ile Thr Asp Asp Gly Thr Ala Ser Gly Thr Leu
305                 310                 315                 320

Lys Glu Ile Lys Arg Phe Tyr Val Gln Asn Gly Lys Val Ile Pro Asn
                325                 330                 335

Ser Glu Ser Thr Trp Ser Gly Val Gly Asn Ser Ile Thr Asn Asp
            340                 345                 350

Tyr Cys Thr Ala Gln Lys Ser Leu Phe Lys Asp Gln Asn Val Phe Ala
            355                 360                 365

Lys His Gly Gly Met Glu Gly Met Gly Ala Ala Leu Ala Gln Gly Met
            370                 375                 380

Val Leu Val Met Ser Leu Trp Asp Asp His Ala Ala Asn Met Leu Trp
385                 390                 395                 400

Leu Asp Ser Asn Tyr Pro Thr Thr Ala Ser Ser Thr Pro Gly Val
                405                 410                 415

Ala Arg Gly Thr Cys Asp Ile Ser Ser Gly Val Pro Ala Asp Val Glu
            420                 425                 430

Ala Asn His Pro Asp Ala Ser Val Val Tyr Ser Asn Ile Lys Val Gly
            435                 440                 445

Pro Ile Gly Ser Thr Phe Asn Ser Gly Gly Ser Asn Pro Gly Gly Gly
            450                 455                 460

Thr Thr Thr Thr Ala Lys Pro Thr Thr Thr Thr Thr Ala Gly Ser
465                 470                 475                 480

Pro Gly Gly Thr Gly Val Ala Gln His Tyr Gly Gln Cys Gly Gly Asn
            485                 490                 495

Gly Trp Gln Gly Pro Thr Thr Cys Ala Ser Pro Tyr Thr Cys Gln Lys
            500                 505                 510

Leu Asn Asp Phe Tyr Ser Gln Cys Leu
            515                 520

<210> SEQ ID NO 23
<211> LENGTH: 1557
<212> TYPE: DNA
<213> ORGANISM: Neosartorya fischeri

<400> SEQUENCE: 23
atgtatcgga agttggccgt catctcggcc ttcttggcca cagctcgtgc tcagcagatt      60
ggtaatctca ctgctgagac tcagccgtct ctgtcctggt ccacttgcac atctggtggc     120
agctgcactt caaagagtgc ctccattact ttggacgcca actggcgctg ggtgcacagt     180
gtcaacggca gcacgaactg ctacaccggc aacacttggg atacatccat ctgtgacact     240
gatacttcct cgcgcagga ctgcgctgtc gacggtgccg actactcggg aacgtacgga     300
attaccacga gcggtaacag cctccgtctg aactttgtca ccggctctaa cgttggctcc     360
cgcacttacc ttatggcgga taagacgcat accagctct tcaacctgct taaccaggag     420
ttcactttca cggttgatgc gtcgaccctg ccgtgcggct gaacggagc tctctacttc     480 gtgtccatgg acgcggatgg tggcgtgagc aagcaaccca caacaaggc tggcgcccag     540 tacggcgttg ggtactgtga cagccagtgt ccccgcgatc tgaagttcat cggcggccag     600
gccaacgttg agggctggca accgtcatcc aacaactcca acgggcct cggaaatcac      660 ggaagctgct gcgcagagct tgatatctgg gaggccaact ccatctccga ggctcttacc     720

```
ccccacccctt gcgatacttc gtcacagact gtatgcaccg gtgatgcctg cggcggaact    780
tactccaatg acagatatgg cggcacttgc gatcccgatg gctgcgactt caacccatac    840
cgcgttggcg tcaccgactt ctacggccct ggcatgacca ttgataccac caagcccgtg    900
accgttgtca cccagttcgt cacgaatgac ggtacctcaa gcggtaccct ttctgagatc    960
agacgatact atgtccagaa tggcaaggtc ttcgcacagc cctcttccaa gattgacgga   1020
atttctggca acgccatcaa ctccgattac tgctccgctg agatttccac tttcggcgga   1080
aacccttctt tcactaagca tggcggcctg caggtgtga gcacagctct taagaatggc    1140
atggttctgg tcatgagtct gtgggatgat tactccgtca acatgctgtg gctggactcc   1200
acctacccga caaacgccac cggtacaccc ggtgccgctc gcggaacctg ctccaccagc   1260
tccggttcac ctaagaccgt cgaagccaac tctcccaacg cccatgtcat cttctccgat   1320
atccgagttg accccttgaa cagcaccttc agtggcagcg gcacttctac ccccggcgga   1380
ggtagcagca ctaccaccag cccgggttcc actaccacta cccccggaag cggaagtgga   1440
agtggagttg cttctcacta cggccagtgc ggcggtcagg gctggactgg ccccacgacc   1500
tgcgccagcg gctttacttg cactgtcata aaccccttact actctcagtg cctgtaa    1557
```

<210> SEQ ID NO 24
<211> LENGTH: 518
<212> TYPE: PRT
<213> ORGANISM: Neosartorya fischeri

<400> SEQUENCE: 24

```
Met Tyr Arg Lys Leu Ala Val Ile Ser Ala Phe Leu Ala Thr Ala Arg
1               5                   10                  15

Ala Gln Gln Ile Gly Asn Leu Thr Ala Glu Thr Gln Pro Ser Leu Ser
            20                  25                  30

Trp Ser Thr Cys Thr Ser Gly Gly Ser Cys Thr Ser Lys Ser Ala Ser
        35                  40                  45

Ile Thr Leu Asp Ala Asn Trp Arg Trp Val His Ser Val Asn Gly Ser
    50                  55                  60

Thr Asn Cys Tyr Thr Gly Asn Thr Trp Asp Thr Ser Ile Cys Asp Thr
65                  70                  75                  80

Asp Thr Ser Cys Ala Gln Asp Cys Ala Val Asp Gly Ala Asp Tyr Ser
                85                  90                  95

Gly Thr Tyr Gly Ile Thr Thr Ser Gly Asn Ser Leu Arg Leu Asn Phe
            100                 105                 110

Val Thr Gly Ser Asn Val Gly Ser Arg Thr Tyr Leu Met Ala Asp Lys
        115                 120                 125

Thr His Tyr Gln Leu Phe Asn Leu Leu Asn Gln Glu Phe Thr Phe Thr
    130                 135                 140

Val Asp Ala Ser Thr Leu Pro Cys Gly Leu Asn Gly Ala Leu Tyr Phe
145                 150                 155                 160

Val Ser Met Asp Ala Asp Gly Gly Val Ser Lys Gln Pro Asn Asn Lys
                165                 170                 175

Ala Gly Ala Gln Tyr Gly Val Gly Tyr Cys Asp Ser Gln Cys Pro Arg
            180                 185                 190

Asp Leu Lys Phe Ile Gly Gly Gln Ala Asn Val Glu Gly Trp Gln Pro
        195                 200                 205

Ser Ser Asn Asn Ser Asn Thr Gly Leu Gly Asn His Gly Ser Cys Cys
    210                 215                 220
```

-continued

```
Ala Glu Leu Asp Ile Trp Glu Ala Asn Ser Ile Ser Glu Ala Leu Thr
225                 230                 235                 240

Pro His Pro Cys Asp Thr Ser Ser Gln Thr Val Cys Thr Gly Asp Ala
            245                 250                 255

Cys Gly Gly Thr Tyr Ser Asn Asp Arg Tyr Gly Gly Thr Cys Asp Pro
        260                 265                 270

Asp Gly Cys Asp Phe Asn Pro Tyr Arg Val Gly Val Thr Asp Phe Tyr
    275                 280                 285

Gly Pro Gly Met Thr Ile Asp Thr Thr Lys Pro Val Thr Val Val Thr
290                 295                 300

Gln Phe Val Thr Asn Asp Gly Thr Ser Ser Gly Thr Leu Ser Glu Ile
305                 310                 315                 320

Arg Arg Tyr Tyr Val Gln Asn Gly Lys Val Phe Ala Gln Pro Ser Ser
            325                 330                 335

Lys Ile Asp Gly Ile Ser Gly Asn Ala Ile Asn Ser Asp Tyr Cys Ser
        340                 345                 350

Ala Glu Ile Ser Thr Phe Gly Gly Asn Pro Ser Phe Thr Lys His Gly
    355                 360                 365

Gly Leu Ala Gly Val Ser Thr Ala Leu Lys Asn Gly Met Val Leu Val
370                 375                 380

Met Ser Leu Trp Asp Asp Tyr Ser Val Asn Met Leu Trp Leu Asp Ser
385                 390                 395                 400

Thr Tyr Pro Thr Asn Ala Thr Gly Thr Pro Gly Ala Ala Arg Gly Thr
            405                 410                 415

Cys Ser Thr Ser Ser Gly Ser Pro Lys Thr Val Glu Ala Asn Ser Pro
        420                 425                 430

Asn Ala His Val Ile Phe Ser Asp Ile Arg Val Gly Pro Leu Asn Ser
    435                 440                 445

Thr Phe Ser Gly Ser Gly Thr Ser Thr Pro Gly Gly Ser Ser Ser Thr
    450                 455                 460

Thr Thr Ser Pro Gly Ser Thr Thr Thr Pro Gly Ser Gly Ser Gly Ser
465                 470                 475                 480

Ser Gly Val Ala Ser His Tyr Gly Gln Cys Gly Gly Gln Gly Trp Thr
            485                 490                 495

Gly Pro Thr Thr Cys Ala Ser Gly Phe Thr Cys Thr Val Ile Asn Pro
        500                 505                 510

Tyr Tyr Ser Gln Cys Leu
        515
```

<210> SEQ ID NO 25
<211> LENGTH: 33
<212> TYPE: DNA
<213> ORGANISM: Artificial Sequence
<220> FEATURE:
<223> OTHER INFORMATION: amorce forward exemple 5

<400> SEQUENCE: 25
tccatcctcg agatgtatcg gaagttggcc gtc          33

<210> SEQ ID NO 26
<211> LENGTH: 35
<212> TYPE: DNA
<213> ORGANISM: Artificial Sequence
<220> FEATURE:
<223> OTHER INFORMATION: amorce reverse exemple 5

```
<400> SEQUENCE: 26
tccatcctcg agttacaggc actgagagta gtaag                                35
```

VARIANTS OF EXOGLUCANASES HAVING IMPROVED ACTIVITY AND USES THEREOF

This application is a U.S. national phase of International Application No. PCT/FR2015/051556, filed Jun. 12, 2015, which claims priority from French Patent application no. FR1455700, filed Jun. 20, 2014, the disclosure of each of which is hereby incorporated by reference in its entirety.

The possibility of producing ethanol from cellulose has received a great deal of attention owing to the availability of large amounts of raw material and also to the advantage of ethanol as a fuel. Cellulose-based natural raw materials for such a process are denoted "biomass". Many types of biomass, for example wood, agricultural residues, herbaceous crops and municipal solid waste, have been considered as potential raw materials for biofuel production. These materials consist mainly of cellulose, hemicellulose and lignin.

Cellulose is a polymer consisting of glucose molecules linked by beta 1,4 linkages, which are very resistant to breakdown or to depolymerization. Once cellulose has been converted to glucose, the latter is easily fermented to biofuel, for example ethanol, using a yeast.

The oldest methods studied for converting cellulose to glucose are based on acid hydrolysis. This process can be carried out in the presence of concentrated or dilute acids. However, several drawbacks, such as the poor recovery of the acid when concentrated acids are used and the low production of glucose in the case of the use of dilute acids, are detrimental to the economic nature of the acid hydrolysis process.

In order to overcome the drawbacks of the acid hydrolysis process, cellulose conversion processes have more recently related to enzymatic hydrolysis, using enzymes of cellulase type. This enzymatic hydrolysis of lignocellulosic biomass (for example, cellulose) has, however, the drawback of being an expensive industrial process. As a result, it is necessary to use increasingly effective cellulase-secreting microorganism strains. In this respect, many microorganisms comprise enzymes which hydrolyze cellulose, such as the fungi *Trichoderma, Aspergillus, Humicola* or *Fusarium* and also bacteria such as *Thermomonospora, Bacillus, Cellulomonas* and *Streptomyces*. The enzymes secreted by these microorganisms possess three different types of activity that are of use in the conversion of cellulose to glucose and can be divided into three groups: endoglucanases, which randomly attack cellulose fibers internally, exoglucanases which will attack the ends of the fibers, releasing cellobiose, and beta-glucosidases which will hydrolyze this cellobiose to glucose. Other classes of enzymes, such as hemicellulases or the recently discovered class of enzymes of polysaccharide monooxygenases, can also play a role in the efficiency of hydrolysis.

There is a strong industrial interest in decreasing the cost of enzymatic hydrolysis, and this decrease involves the use of a reduced dose of enzymes and thus of cocktails of enzymes that are more efficient. Consequently, several patent applications describe natural enzymes with capacities that are greater than those of *Trichoderma reesei*, or variants improved by genetic engineering. Mention may be made of patent applications US2010304464, WO 2010/066411 and WO 2013/029176 relating to exoglucanses, applications WO 2007/109441, WO 2012/149192 and WO 2010/076388 relating to endoglucanases, applications WO 2010/029259, WO 2010/135836 or WO 2010/022518 relating to beta-glucosidases, or else applications WO 12135659 and WO 12149344 relating to polysaccharide monooxygenases.

Enzymes which hydrolyze lignocellulosic biomass are classified in the CAZy system (Cantarel, B. L., Coutinho, P. M., Rancurel, C., Bernard, T., Lombard, V., & Henrissat, B. (2009). The Carbohydrate-Active EnZymes database (CAZy): an expert resource for Glycogenomics. Nucleic acids research, 37, D233-8) on the basis of mainly structural criteria. Exoglucanases can belong to the GH 6, 7, 9, 48 and 74 families.

In order for lignocellulosic biomass hydrolysis to be efficient and economically profitable, the enzymatic mixture must comprise balanced proportions of enzymes having various enzymatic activities, inter alia, but not exclusively, of the exoglucanase, endoglucanase, xylanase and beta-glucosidase type. By way of example, in the native mixtures of *Trichoderma reesei*, the presence of 60-70% of exoglucanases, 15-20% of endoglucanases, a few percent of hemicellulases and approximately 5-10% of beta-glucosidases is generally noted. This mixture is suitable for hydrolyzing the majority of pretreated substrates (for example of the type wheat straw steam-exploded under acid conditions) with acceptable yields. The already considerable proportion of exoglucanases in the mixture indicates that it will be difficult to increase the amount of these enzymes without penalizing the other endoglucanase, hemicellulase and glucosidase activities. The *Trichoderma reesei* genome comprises two exoglucanases, one derived from family 6 (CBH2, cel6a) and the other derived from family 7 (CBH1, Cel7a). These two exoglucanases hydrolyze to cellobiose respectively the non-reducing (EC3.2.1.176) and reducing (EC3.2.1.91) ends of cellulose.

The hydrolysis and the fermentation can be carried out according to various schemes. The most common consists of separate hydrolysis and fermentation (SHF). This method makes it possible to optimize each step by maintaining the optimal reaction conditions. This fermentation is carried out extemporaneously, at a temperature of between approximately 28° C. and approximately 30° C., whereas the hydrolysis generally takes place at a temperature of at least 45° C. However, in SHF, the sugars released at the end of the reaction are present at very high concentration and cause inhibition of the enzymes, slowing down the efficiency of the process. In order to avoid these drawbacks, another type of process can be envisioned. In SSF (Simultaneous Saccharification and Fermentation), the two steps (hydrolysis and fermentation of hexoses) take place simultaneously, preventing sugar accumulation at concentrations that are inhibitory for the enzymes. The investment costs are also reduced by virtue of the use of a single reactor. The rate of hydrolysis is higher as a consequence of the absence of inhibition, since the sugars released are used immediately for fermentation to ethanol. In this method, the temperature of the reactor necessarily constitutes a compromise between the optimal temperatures of hydrolysis and of fermentation, typically between approximately 30° C. and approximately 35° C. However, at such a temperature, the activity of the cellulolytic enzymes is decreased by approximately 30%.

SSF also allows the expression of enzymes that degrade cellulose in the organism fermenting the sugars, thereby making it possible to limit, or in an extreme case to eliminate, recourse to enzymes produced during a separate step.

Consequently, the obtaining of enzymes which maintain an exoglucanase activity that is efficient at the optimal temperatures of hydrolysis and fermentation (i.e. between 30° C. and 50° C.), while at the same time keeping the proportion of all of the enzymes of the mixture, would be a significant gain for the process of converting lignocellulosic biomass to biofuel.

The inventors have developed a polypeptide having an improved exoglucanase activity, in particular compared with the exoglucanase activity of the CBH1 reference protein of sequence SED ID NO: 2. CBH1 corresponds to exoglucanase 1 from *Trichoderma reesei*.

In this perspective, the applicants have, to their great credit, found, after numerous research studies, an isolated or purified polypeptide having an improved exoglucanase activity compared with the exoglucanase activity of the CBH1 reference protein (SEQ ID NO: 2).

The invention thus relates to a polypeptide chosen from the group consisting of:

i. an amino acid sequence chosen from SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20; and ii. an amino acid sequence having a percentage of residues that are identical compared with one of the sequences SEQ ID NO: 6, SEQ ID NO: 8, SEQ ID NO: 10, SEQ ID NO: 12, SEQ ID NO: 14, SEQ ID NO: 16, SEQ ID NO: 18 or SEQ ID NO: 20 (or percentage identity), of at least 70%, preferentially of at least 75%, 80%, 85%, 90%, 95%, 98% or 99%.

Preferably, the polypeptide as described above is characterized in that its expression in a fermentative organism is at least equal to the expression of the CBH1 reference protein (SEQ ID NO: 2).

According to the invention, the percentage identity of a given sequence relative to SEQ ID NO: 4, 6, 8, 10, 12, 14, 16, 18 or 20 corresponds to the number of residues that are identical between this given sequence and SEQ ID NO: 4, 6, 8, 10, 12, 14, 16, 18 or 20, divided by the number of residues in SEQ ID NO: 4, 6, 8, 10, 12, 14, 16, 18 or 20.

In one preferred embodiment, the polypeptide of the invention has an exoglucanase activity which is improved by at least 10%, preferentially by at least 20%, preferentially by at least 30%, even more preferentially by at least 40%, at a temperature of approximately 35° C. and/or of approximately 50° C., compared with the exoglucanase activity of the CBH1 polypeptide of amino acid sequence SEQ ID NO: 2.

Those skilled in the art will for example be able to determine the increase or in other words the improvement in the enzymatic activity either using a substrate such as the cellulose Avicel®, the cellulose PASC or "Walseth", or with a chromogenic substrate (p-nitrophenyl glycoside), for example pNP lactoside. The enzymatic activity will be respectively revealed by colorimetric assay of the reducing sugars or else of the nitrophenol released.

An example of a protocol that those skilled in the art will be able to use for determining whether a polypeptide according to the invention has an enzymatic activity that is improved compared with that of the CBH1 reference protein (SEQ ID NO: 2), is the following:

preparation of a stock culture of *Y. lipolytica* expressing a recombinant enzyme according to the invention, overnight at 28° C.;
inoculation of an expression medium with a volume of stock culture making it possible to have an OD at 600 nm equal to 0.2 at the beginning of culture;
culture of said cells at 28° C. for 96 hours;
centrifugation at 8000 rpm for 5 minutes;
incubation of 100 µl of supernatant with 100 µl of 0.1 M citrate phosphate buffer, pH 6, containing 1% of reduced cellodextrins (CDs), for 24 hours at 35° C. and 50° C.;
removal of 100 µl of reaction;
addition of 100 µl of DNS reagent;
incubation for 5 minutes at 100° C.;
incubation for 3 minutes on ice;
centrifugation for 10 minutes at 3000 rpm;
reading of the OD at 540 nm on 150 µl.

Table 1 below comprises the identifications of the nucleic and peptide sequences for CBH1 from *T. reesei* ("wild-type"), the putative exoglucanases from *Talaromyces stipitatus* (TS) and from *Neosartorya ficheri* (NF), and also for the polypeptides and nucleotides of the invention.

TABLE 1

| Improved clones and parent genes | | |
|---|---|---|
| Clones | Nucleic acid | Polypeptide |
| cbh1 (wild-type) | SEQ ID NO: 1 | SEQ ID NO: 2 |
| 32F9 | SEQ ID NO: 3 | SEQ ID NO: 4 |
| 64C2 | SEQ ID NO: 5 | SEQ ID NO: 6 |
| 130G9 | SEQ ID NO: 7 | SEQ ID NO: 8 |
| 224C11 | SEQ ID NO: 9 | SEQ ID NO: 10 |
| 225B11 | SEQ ID NO: 11 | SEQ ID NO: 12 |
| 242D11 | SEQ ID NO: 13 | SEQ ID NO: 14 |
| 453E8 | SEQ ID NO: 15 | SEQ ID NO: 16 |
| B | SEQ ID NO: 17 | SEQ ID NO: 18 |
| 91D9 | SEQ ID NO: 19 | SEQ ID NO: 20 |
| NF gene | SEQ ID NO: 21 | SEQ ID NO: 22 |
| TS gene | SEQ ID NO: 23 | SEQ ID NO: 24 |

A subject of the invention is also a purified or isolated nucleic acid encoding at least one polypeptide as described above.

Preferably, said purified or isolated nucleic acid can be chosen from the following sequences: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17 and SEQ ID NO: 19.

According to the invention, the nucleic acid as described above may be functionally linked to a promoter, a terminator or any other sequence required for its expression in a host cell.

The invention also relates to a vector comprising at least one nucleic acid as described above.

According to the invention, the term "vector" is intended to mean any DNA sequence into which it is possible to insert foreign nucleic acid fragments, the vectors making it possible to introduce foreign DNA into a host cell. As vectors, mention may be made, non-exhaustively, of: plasmids, cosmids, yeast artificial chromosomes (YACs), bacterial artificial chromosomes (BACs), P1 bacteriophage-derived artificial chromosomes (PACs) or virus-derived vectors.

The vector according to the invention may also carry a selectable marker. The term "selectable marker" is intended to mean a gene of which the expression confers on the cells that contain it a characteristic making it possible to select them. It is for example an antibiotic resistance gene.

A subject of the invention is also an isolated host cell comprising either at least one of the polypeptides as described above, or at least one of the nucleic acids as described above, or at least one of the vectors as described above.

Those skilled in the art will be able to introduce one of the polypeptides, one of the nucleic acids or one of the vectors as described above into the host cell by well-known conventional methods. For example, mention may be made of calcium chloride treatment, electroporation, and the use of a particle gun.

According to one embodiment, those skilled in the art will be able to introduce, into the host cell and by conventional methods, several copies of a nucleic acid encoding a polypeptide having an improved exoglucanase activity according to the invention.

According to one embodiment, the isolated host cell as described above is chosen from *Trichoderma, Aspergillus, Neurospora, Humicola, Myceliophthora, Chrysosporium, Penicillium, Fusarium, Thermomonospora, Bacillus, Pseudomonas, Escherichia, Clostridium, Cellulomonas, Streptomyces, Yarrowia, Pichia* and *Saccharomyces*.

According to one preferred embodiment, the isolated host cell as described above is chosen from *Trichoderma reesei, Trichoderma viridae, Trichoderma koningii, Aspergillus niger, Aspergillus nidulans, Aspergillus wentii, Aspergillus oryzae, Aspergillus phoenicis, Myceliophthora thermopila, Chrysosporium lucknowense, Neurospora crassa, Humicola grisae, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

According to one preferred embodiment, the isolated host cell as described above is chosen from *Trichoderma reesei* and *Saccharomyces cerevisiae*.

A subject of the invention is also the use of at least any one of the polypeptides described above, for cellulose hydrolysis.

A subject of the invention is also the use of at least any one of the polypeptides described above, for biofuel production.

According to the invention, the term "biofuel" can be defined as being any product resulting from the conversion of biomass and that can be used for energy purposes. Firstly, and without wishing to be limited thereto, mention may be made, by way of example, of biogases, products that can be incorporated (optionally after subsequent conversion) into a fuel or which can be a fuel in their own right, such as alcohols (ethanol, butanol and/or isopropanol depending on the type of fermentative organism used), solvents (acetone), acids (butyric), lipids and their derivatives (short-chain or long-chain fatty acids, fatty acid esters), and also hydrogen.

Preferably, the biofuel according to the invention is an alcohol, for example ethanol, butanol and/or isopropanol. More preferentially, the biofuel according to the invention is ethanol.

In another embodiment, the biofuel is biogas.

In another embodiment, the product is a molecule that is advantageous in the chemical industry, for instance another alcohol, such as 1,2-propanediol, 1,3-propanediol, 1,4-propanediol or 2,3-butanediol, organic acids such as acetic acid, propionic acid, acrylic acid, butyric acid, succinic acid, malic acid, fumaric acid, citric acid or itaconic acid, or hydroxy acids such as glycolic acid, hydroxypropionic acid or lactic acid.

An embodiment for producing an enzymatic cocktail that is of use for lignocellulose hydrolysis is described below.

The strains of filamentous fungi, preferably *Trichoderma*, more preferentially *T. reesei*, capable of expressing at least one polypeptide according to the invention are cultured in fermenters, in the presence of a carbon-based substrate, such as lactose or glucose, chosen for the growth of the microorganism. In one embodiment, this carbon-based substrate, depending on its nature, is introduced into the fermenter before sterilization or is sterilized separately and introduced into the fermenter after sterilization of the latter so as to obtain an initial concentration of 20 to 35 g/l.

An aqueous solution containing the substrate chosen for the enzyme production is then added. An enzymatic composition which acts on lignocellulosic biomass, produced by the fungi is finally recovered by filtration of the culture medium. This composition contains in particular the beta-glucosidase, the endoglucanase and the exoglucanase according to the invention.

In one embodiment, the aqueous solvent containing the substrate chosen for the enzyme production is prepared at the concentration of 200-250 g/l. This solution also preferably contains an inducer substrate such as lactose. This aqueous solution is injected after exhaustion of the initial carbon-based substrate so as to provide an optimized amount, of between 35 and 45 mg/g of cells (fed batch). During this fed batch phase, the residual concentration of sugar in the culture medium is less than 1 g/l and the enzymes which act on lignocellulosic biomass are secreted by the fungus. Said enzymes can be recovered by filtration of the culture medium.

A subject of the invention is an enzymatic composition capable of acting on lignocellulosic biomass, said enzymatic composition being produced by filamentous fungi and comprising at least any one of the polypeptides described above.

The term "filamentous fungi" is intended to mean in particular *Trichoderma*, more preferentially *T. reesei*.

Finally, a subject of the invention is a process for producing biofuel from biomass, comprising the following successive steps:

the biomass to be hydrolyzed is suspended in an aqueous phase;
the lignocellulosic biomass is hydrolyzed in an presence of an enzymatic composition as described above so as to produce a hydrolysate containing glucose;
the glucose of the hydrolysate is fermented in the presence of a fermentative organism so as to produce a fermentation must;
the biofuel is separated from the fermentation must.

In one embodiment, the biomass to be hydrolyzed is suspended in an aqueous phase in an amount of from 6% to 40% of solids, preferably 20% to 30%. The pH is adjusted to between 4 and 5.5, preferably between 4.8 and 5.2, and the temperature to between 40 and 60° C., preferably between 45 and 50° C. The hydrolysis reaction is initiated by adding the enzymatic composition which acts on lignocellulosic biomass; the amount normally used is from 10 to 30 mg of excreted proteins per gram of pretreated substrate or less. The reaction generally lasts from 15 to 48 hours. The reaction is followed by assaying of the sugars released, in particular glucose.

The sugar solution is separated from the non-hydrolyzed solid fraction, essentially consisting of lignin, by filtration or centrifugation and then treated in a fermentation unit.

After the fermentation step, the biofuel is separated from the fermentation must for example by distillation.

Another subject of the invention is a process for producing biofuel from biomass, characterized in that it comprises the following successive steps:

the biomass to be hydrolyzed is suspended in an aqueous phase;
an enzymatic composition which acts on lignocellulosic biomass as defined above and a fermentative organism are simultaneously added to the suspension and the mixture is fermented so as to produce a fermentation must;

the biofuel is separated from the fermentation must.

Preferably, the enzymatic composition and the fermentative organism are added simultaneously and then incubated at a temperature of between 30° C. and 35° C. so as to produce a fermentation must.

According to this embodiment, the cellulose present in the biomass is converted to glucose, and at the same time, in the same reactor, the fermentative organism (for example a yeast) converts the glucose to the final product according to an SSF (Simultaneous Saccharification and Fermentation) process known to those skilled in the art. Depending on the metabolic and hydrolytic capacities of the fermentative organism, it may be necessary to add a more or less significant amount of exogenous cellulolytic mixture in order for the operation to proceed correctly.

In another embodiment, the fermentative organism produces the polypeptide which is the subject matter of the invention by secretion or at the surface of its cell, optionally together with other enzymes which act on lignocellulosic biomass, thus limiting or eliminating the need for enzymes produced by the filamentous fungus. Preferably, the fermentative organism is a host cell as described above.

Preferably, the host cells producing the enzymatic composition and/or the fermentative organism are added and then incubated at a temperature of between 30° C. and 35° C. so as to produce a fermentation must.

The use of the polypeptide having a better exoglucanase activity according to the present invention thus has the advantage of obtaining a better glucose production yield while at the same time using less enzyme than previously, thereby also having an economic advantage.

Other aspects, subjects, advantages and features of the invention will be presented on reading the non-restrictive description which follows and which describes preferred embodiments of the invention, given by means of examples and of FIGS. 1 to 8.

EXAMPLES

Example 1: Preparation of DP 3-11 Reduced Cellodextrins

1—Cellulose Hydrolysis
Adapted from Y-H. Percival Zhang, L. R. Lynd Analytical Biochemistry 322 (2003), 225-232.

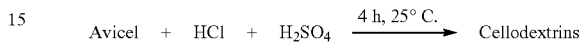

$$\text{Avicel} + \text{HCl} + \text{H}_2\text{SO}_4 \xrightarrow{\text{4 h, 25° C.}} \text{Cellodextrins}$$

20 g of cellulose (Avicel, CAS Number 9004-34-6, Sigma-Aldrich Saint-Quentin Fallavier) are added portionwise and with vigorous stirring to 160 ml of a hydrochloric acid solution cooled to 0° C. Precooled sulfuric acid is added to the solution in several steps (4×10 ml). The reaction is kept stirring for four hours at 24° C. before being poured into 1.8 l of acetone cooled to −20° C.

After two hours of stirring, the precipitate is filtered off, taken up in 400 ml of cooled acetone and then again filtered. The solid is then taken up in 600 ml of water, and then stirred overnight in order to dissolve the cellodextrins (CDs). After the solid has been filtered off, the soluble fraction containing the cellodextrins is neutralized with 300 g of Amberlite IRA 400 OH⁻ resin and then lyophilized. The lyophilisate is then resuspended in 500 ml of methanol in the presence of ultrasound for 30 minutes in order to dissolve the low-molecular-weight sugars, before being filtered and then lyophilized again so as to give 6.8 g of DP 3-11 cellodextrins. For the screening, it was chosen to work with substrates of the highest possible molecular weight in order to mimic as closely as possible the structure of cellulose. However, high-molecular-weight cellodextrins are not soluble, which prevents good reproducibility of the tests.

A range of cellodextrins of DP 5-7 was therefore chosen, which represents a good compromise between the high molecular weight required and the solubility of the cellodextrins.

Figure 1:
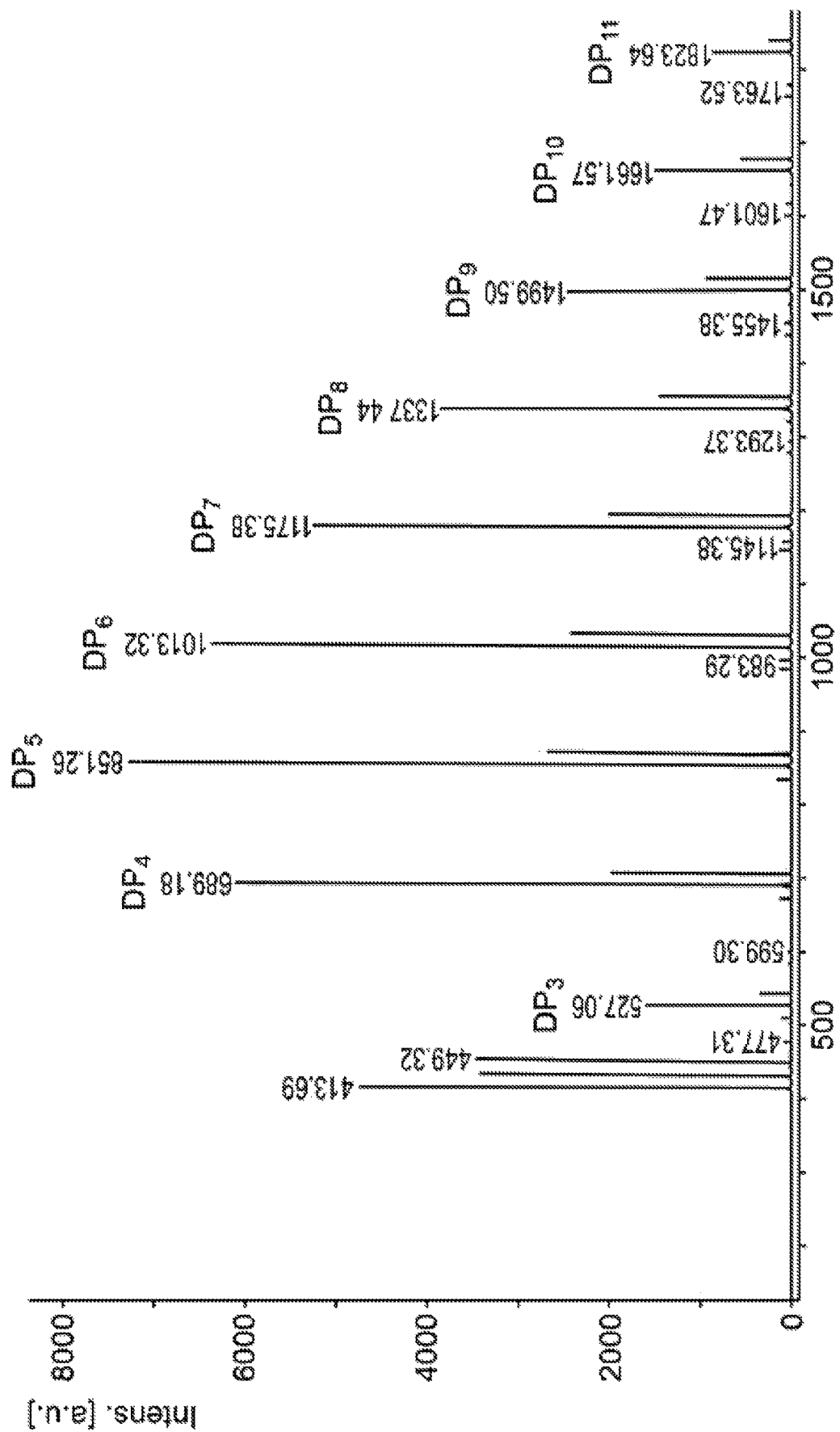
FIG. 1 is a MALDI-TOF mass spectrum representing the DP3 to DP11 cellodextrins used for the screening.

FIG. 1 presents a MALDI-TOF mass spectrum typically obtained according to the process described above.

FIG. 1 shows that the isolated oligosaccharides are predominantly of DP 5-7.

2—Cellodextrin Reduction
400 mg of sodium borohydride are added to 2 g of DP 3-11 cellodextrins diluted in 120 ml of water. After three hours with stirring at ambient temperature, the solution is neutralized by adding Amberlite H⁺ IR 120 resin, filtered, and then lyophilized, so as to give 2 g of quantitatively reduced cellodextrins (C. Schou, G. Rasmussen, M-B. Kaltoft, B. Henrissat, M. Schulein Eur. J. Biochem. 217, 947-953 (1993)).

Assaying of the isolated cellodextrins with BCA (bicinchoninic acid) makes it possible to verify the total reduction of the ends (Y.-H. Percival Zhang, L. R. Lynd Biomacromolecules 2005, 6, 1510-1515).

Example 2: Evolution by L-Shuffling

The sequence of the cellobiohydrolase 1 gene (cbh1, SEQ ID NO: 1) from *Trichoderma reesei* was subjected to a round of L-shuffling according to the patented process described in patent EP 1 104 457 with the genes of a cellobiohydrolase from *Talaromyces stipitatus* ATCC 10500 (TS, SEQ ID NO: 23) and of a cellobiohydrolase from *Neosartorya fischeri* NRRL 181 (NF, SEQ ID NO: 21) having respectively 62% and 61% homology with the cbh1 parental gene.

1—High-Throughput Screening

A high-throughput screening test was developed in order to select the best clones resulting from the L-shuffling, i.e. those exhibiting at least 20% improvement in the cellobiohydrolase activity compared with the cbh1 reference enzyme (SEQ ID NO: 2).

The high-throughput screening test was carried out according to the following steps:
- isolation on agar of the clones of *Y. lipolytica* expressing the L-shuffling variants of the enzyme according to the invention and preculturing in YNB casa medium (yeast nitrogen base 1.7 g/l, NH$_4$Cl 10 g/l, glucose 10 g/l, casamino acids 2 g/l, pH 7) of said colonies for 36 hours at 28° C.;
- inoculation of a YTD medium (yeast extract 10 g/l, tryptone 20 g/l, glucose 2.5 g/l, pH 6.8) supplemented with tetracycline at 12.5 µg/ml at 5% with the preculture and then incubation for 20 hours at 28° C.;
- inoculation of the expression medium containing the inducer (oleic acid) in an amount of 20 g/l at 10% with the previous culture and then incubation for 96 hours at 28° C.;
- centrifugation for five minutes at 1500 rpm;
- removal of 100 µl of supernatant;
- addition of 100 µl of reduced CDs at 1 g/l in 0.1 M citrate phosphate buffer at pH 6;
- incubation for 17 hours at 50° C.;
- centrifugation for five minutes at 2500 rpm;
- removal of 80 µl of supernatant;
- addition of 80 µl of DNS reagent;
- incubation for 12 minutes at 105° C. and then five minutes on ice;
- reading of the optical density (OD) at 540 nm on 120 µl.

Under these screening conditions, an improvement in the cellobiohydrolase activity (increase in the OD at 540 nm) compared with the cbh1 reference enzyme (SEQ ID NO: 2) was found in several clones, including in particular the 32F9, 64C2, 130G9, 224C11, 225B11 and 453E8 clones (respectively SEQ ID NO: 4, 6, 8, 10, 12 and 16).

2—Determination of the Improvement in the Cellobiohydrolase Activity 2-1/ On the Reduced-Cellodextrin Substrate In order to estimate the relative kcat of the variants selected in the first round of L-shuffling with respect to the cbh1 reference enzyme (SEQ ID NO: 2), the following process is carried out:
- preparation of a stock culture of *Y. lipolytica* expressing a recombinant enzyme according to the invention, overnight at 28° C.;
- inoculation of an expression medium with a volume of stock culture making it possible to have an OD at 600 nm equal to 0.2 at the beginning of the culture;
- culture of said cells at 28° C. for 96 hours;
- centrifugation at 8000 rpm for five minutes;
- incubation of 100 µl of supernatant with 100 µl of 0.1 M citrate phosphate buffer, pH 6, containing 1% of reduced CDs, for 24 hours at 35° C. and 50° C.;
- removal of 100 µl of reaction;
- addition of 100 µl of DNS reagent;
- incubation for five minutes at 100° C.;
- incubation for three minutes on ice;
- centrifugation for 10 minutes at 3000 rpm;
- reading of the OD at 540 nm on 150 µl.

According to the invention, the calculation of the kcats is carried out in the following way:
- plotting the curve of the ODs at 540 nm as a function of the amount of protein of interest (in nM);
- subtracting the value of the negative control;
- dividing by the direction coefficient of the glucose standard rate (various amounts of glucose are revealed with the DNS);
- dividing by the reaction time (1440 minutes).

Table 2 gives the value of the kcats and also the improvement factor obtained for the 32F9, 64C2, 130G9, 224C11, 225B11 and 453E8 clones (respectively SEQ ID NOs: 4, 6, 8, 10, 12 and 16) compared with the cbh1 reference protein (SEQ ID NO: 2) under these experimental conditions.

TABLE 2 improvement in the cellobiohydrolase activity on reduced CDs

|  | Clone | 35° C. Kcat (min$^{-1}$) | 50° C. Kcat (min$^{-1}$) | Improvement factor |
|---|---|---|---|---|
| First-round clones | 32F9 | 0.0024 | 0.0116 | 1.5 |
|  | 64C2 | 0.0165 | 0.019 | 2.4 |
|  | 130G9 | 0.0031 | 0.0071 | 0.9 |
|  | 224C11 | 0.0032 | 0.0112 | 1.4 |
|  | 225B11 | 0.0022 | 0.0092 | 1.2 |
|  | 453E8 | 0.0043 | 0.019 | 2.4 |
| Reference protein | cbh1 | 0 | 0.008 | 1 |

At 35° C., the improvement factor compared with the cbh1 reference enzyme (SEQ ID NO: 2) could not be calculated because, under these experimental conditions, the activity of cbh1 is not measurable. The enzymatic activity of the 32F9, 64C2, 224C11, 225B11 and 453E8 clones is improved at 35° C. and 50° C. compared with the enzymatic activity of the cbh1 reference enzyme (SEQ ID NO: 2). The enzymatic activity of the 130G9 enzyme (SEQ ID NO: 8) is improved at 35° C. compared with the enzymatic activity of the cbh1 reference enzyme (SEQ ID NO: 2).

2-2/ On the Avicel Substrate

The improvement in activity of the 32F9, 64C2, 130G9, 224C11, 225B11 and 453E8 clones (respectively SEQ ID NOs: 4, 6, 8, 10, 12 and 16) was then measured with a second substrate: Avicel.

The activity of these clones was determined by measuring the end-point OD at 540 nm according to the protocol described above. The reduced-cellodextrin substrate is replaced with the Avicel substrate at the same concentration. The activity test is carried out with 100 µl of culture supernatant containing the protein of interest, for 48 hours.

Table 3 presents the value of the ODs at 540 nm after subtraction of the OD value obtained with the negative control and also the improvement factor of the 32F9, 64C2, 130G9, 224C11, 225B11 and 453E8 clones (respectively SEQ ID NOs: 4, 6, 8, 10, 12 and 16) compared with the cbh1 reference enzyme (SEQ ID NO: 2) under these experimental conditions.

TABLE 3 improvement in the cellobiohydrolase activity on Avicel

|  | Clone | 35° C. | | 50° C. | |
|---|---|---|---|---|---|
|  |  | Delta OD 540 nm | Improvement factor | Delta OD 540 nm | Improvement factor |
| First-round clones | 32F9 | 0.023 | 1.6 | 0.033 | 1.5 |
|  | 64C2 | 0.007 | 0.5 | 0.0176 | 0.8 |
|  | 130G9 | 0.076 | 5.4 | 0.065 | 3.0 |
|  | 224C11 | 0.014 | 1.0 | 0.046 | 1.0 |
|  | 225B11 | 0.008 | 0.6 | 0.009 | 0.4 |
|  | 453E8 | 0.029 | 2.1 | 0.05 | 2.3 |
| Reference protein | cbh1 | 0.014 | 1 | 0.022 | 1 |

These results show an improvement in the enzymatic activity, compared with the cbh1 reference enzyme (SEQ ID NO: 2) for the 32F9, 130G9 and 453E8 clones (respectively SEQ ID NO: 4, SEQ ID NO: 8 and SEQ ID NO: 16) at 35° C. and 50° C.

Example 3: Evolution by Recombination

The 32F9, 130G9 and 453E8 genes (respectively SEQ ID NO: 3, SEQ ID NO: 7 and SEQ ID NO: 15) were chosen because the enzymes that they encode are improved on reduced CDs and Avicel. The 242D11 gene (SEQ ID NO: 13) was selected because its sequence differs from that of the 32F9, 130G9 and 453E8 clones and thus makes it possible to improve the sequence diversity. The 32F9, 130G9, 453E8 and 242D11 genes were recombined to generate new mutants. The activity of the mutants obtained was first of all evaluated with the reduced-CD substrate according to the protocol described in section 2-1 of example 2.

1—Determination of the Improvement in the Cellobiohydrolase Activity 1-1/ On the Reduced-Cellodextrin Substrate Mutant B (SEQ ID NO: 18) has an improved cellobiohydrolase activity (increase in the OD at 540 nm) compared with the 453E8 variant (SEQ ID NO: 16). The 453E8 variant is the best variant resulting from the evolution by L-shuffling.

Table 4 presents the value of the kcats and also the improvement factor obtained for clone B compared with the 453E8 protein (SEQ ID NO: 16) under these experimental conditions. The kcats are calculated according to the protocol described in section 2-1 of example 2.

TABLE 4 improvement in the cellobiohydrolase activity on reduced cellodextrins

|  | Clone | 35° C. | | 50° C. | |
|---|---|---|---|---|---|
|  |  | Kcat (min$^{-1}$) | Improvement factor | Kcat (min$^{-1}$) | Improvement factor |
|  | B | 0.0054 | 2.2 | 0.0136 | 0.9 |
| Reference protein | 453E8 | 0.0025 | 1 | 0.015 | 1 |

The result show an improvement in the enzymatic activity compared with the reference enzyme (SEQ ID NO: 16) for clone B (SEQ ID NO: 18) at 35° C.

1-2/ On the Avicel Substrate

The improvement in activity of clone B was then confirmed with a second substrate: Avicel.

The activity of these clones was determined by measuring the end-point OD at 540 nm according to the protocol described in section 2-2 of example 2.

Table 5 presents the value of the kcats and also the improvement factor obtained for clone B compared with the 453E8 reference protein (SEQ ID NO: 16) under these experimental conditions.

TABLE 5 improvement in the cellobiohydrolase activity on Avicel

|  | Clone | 35° C. | | 50° C. | |
|---|---|---|---|---|---|
|  |  | Delta OD 540 nm | Improvement factor | Delta OD 540 nm | Improvement factor |
|  | B | 0.041 | 2.15 | 0.008 | 0.2 |
| Reference protein | 453E8 | 0.019 | 1 | 0.039 | 1 |

These results show an improvement in the enzymatic activity compared with the 453E8 enzyme (SEQ ID NO: 16) for clone B (SEQ ID NO: 18) at 35° C.

Example 4: Evolution by Evosight

In order to improve the cellobiohydrolase activity, the Evosight strategy (patent application WO 2006/003298) was applied to the 453E8 mutant (SEQ ID NO: 15), the best variant resulting from the L-shuffling.

1—High-Throughput Screening

The high-throughput screening test used to select the best clones, i.e. those exhibiting at least 20% improvement in cellobiohydrolase activity compared with the 453E8 enzyme (SEQ ID NO: 16), is the same as that described in section 1 of example 2. The variants generated by Evosight are compared with the 453E8 clone (SEQ ID NO: 16) because it is the best clone resulting from the L-shuffling.

Under these screening conditions, an improvement in the cellobiohydrolase activity (increase in the OD at 540 nm) compared with the 453E8 enzyme (SEQ ID NO: 16) was found in several clones, in particular the 91D9 clone (SEQ ID NO: 20).

2—Determination of the Improvement in the Cellobiohydrolase Activity 2-1/ On the Reduced-Cellodextrin Substrate The protocol used to determine the relative kcat of the 91D9 clone (SEQ ID NO: 20) compared with the 453E8 enzyme (SEQ ID NO: 16) is identical to that described in section 2-1 of example 1.

Table 6 presents the value of the kcats and also the improvement factor obtained for the 91D9 clone compared with the 453E8 enzyme (SEQ ID NO: 16) under these experimental conditions.

TABLE 6 improvement in the cellobiohydrolase activity on reduced cellodextrins

|  | Clone | 35° C. | | 50° C. | |
|---|---|---|---|---|---|
|  |  | Kcat (min$^{-1}$) | Improvement factor | Kcat (min$^{-1}$) | Improvement factor |
|  | 91D9 | 0.0072 | 2.88 | 0.0174 | 1.2 |
| Reference protein | 453E8 | 0.0025 | 1 | 0.015 | 1 |

These results show an improvement in the enzymatic activity compared with the 453E8 enzyme (SEQ ID NO: 16) for the 91D9 clone (SEQ ID NO: 20) at 35° C. and 50° C.

2-2/ On the Avicel Substrate

The improvement in activity of the 91D9 clone was then confirmed with a second substrate: Avicel.

The activity of this clone was determined by measuring the end-point OD at 540 nm according to the protocol described in section 2-2 of example 2.

Table 7 presents the value of the kcat and also the improvement factor obtained for the 91D9 clone compared with the 453E8 protein (SEQ ID NO: 16) under these experimental conditions.

TABLE 7 improvement in the cellobiohydrolase activity on Avicel

|  | Clone | 35° C. | | 50° C. | |
| --- | --- | --- | --- | --- | --- |
|  |  | Delta OD 540 nm | Improvement factor | Delta OD 540 nm | Improvement factor |
|  | 91D9 | 0.05 | 2.63 | 0.004 | 0.2 |
| Reference protein | 453E8 | 0.019 | 1 | 0.039 | 1 |

These results show an improvement in the enzymatic activity compared with the 453E8 enzyme (SEQ ID NO: 16) for the 91D9 enzyme (SEQ ID NO: 20) at 35° C.

Example 5: Cloning of the Exoglucanase 1 Variants 130G9 and 453E8 in the *T. Reesei* CL847 ΔCBH1 Strain The 130G9 and 453E8 variants are clones resulting from the L-shuffling. Each variant was cloned into a *T. reesei* CL847 ΔCBH1 strain.

The coding sequences of the 130G9 and 453E8 variants were amplified by PCR using the following oligonucleotides:

```
For:
                                            (SEQ ID NO: 25)
TCCATCctcgagatgtatcggaagttggccgtc Rev:
                                            (SEQ ID NO: 26)
TCCATCctcgagttacaggcactgagagtagtaag
```

The fragments obtained were digested with XhoI and then cloned into an expression vector between the cbh1 promoter and terminator, according to methods known to those skilled in the art (Wang et al., 2012, Microb Cell Fact. 2012 Jun. 18; 11:84. doi: 10.1186/1475-2859-11-84). The selectable marker of the vector is phleomycin (Calmels et al., 2011, Curr Genet. 1991 September; 20(4):309-14).

The strain used for the construction is a CL847 strain (Durand et al., 1988, Enz. Microb Technol, 10, 341-346), the CBH1 gene of which has been removed beforehand according to a method known to those skilled in the art (Suominen et al., MGG, 1993, 241; 523-530) to give the CL847ΔCBH1 strain. Protoplasts of the *T. reesei* CL847ΔCBH1 strain were transformed according to a conventional method known to those skilled in the art, by calcium and PEG shock, with 5 µg of the DNA fragment containing the sequences encoding the 130G9 or 453E8 variant. The clones thus obtained were selected on PDA/sucrose selective medium containing 50 g/ml of phleomycin. The number of clones obtained after purification and isolation is presented in table 8.

TABLE 8

Selection of the clones having integrated the variant of interest

| Variant name | Number of clones subcultured after transformation | Number of pure clones isolated |
| --- | --- | --- |
| 130G9 | 231 | 19 |
| 453E8 | 189 | 11 |

The activity of the isolated pure clones is screened on cellulose dishes coupled with analysis of the secretome on a 2D gel.

The screening medium, termed "Walseth Cellulose" medium, is prepared in the following way:

250 ml/l of "4N" medium (KOH 3.32 g/l, 85% $H_3PO_4$ 5 ml/l, $(NH_4)_2SO_4$ 5.6 g/l, $MgSO_4.7H_2O$ 1.2 g/l, $CaCl_2.2H_2O$ 1.2 g/l, $Na_2HPO_4.12H_2O$: 0.23 g/l, pH adjusted to 1.5 with $H_2SO_4$);

1 ml/l of a solution of trace elements ($FeSO_4.7H_2O$ 30 g/l, $Co(NO_3)_2.6H_2O$ 9 g/l, $MnSO_4.1H_2O$ 6.4 g/l, $ZnSo_4.7H_2O$ 8.4 g/l, boric acid 0.4 g/l, sodium molybdate 1.04 g/l, pH adjusted to 1.5 with $H_3PO_4$);

2 g/l of peptone;

2 g/l of agar;

50 g/l of 8% cellulose prepared according to the Walseth method (Walseth, 1952, Tappi, 225; 228-232).

The whole mixture is homogenized using a homogenizer (Ultra Turrax, Ika, Germany) for five minutes. The pH is adjusted to 6.0 with a 3 M KOH solution. The medium obtained is autoclaved at 110° C. for 30 minutes. When the temperature of the medium is 50° C., the phleomycin is added in an amount of 50 µg/ml. The medium is then transferred into the Petri dishes in an amount of 20 ml/dish. The solidification is monitored until complete setting of the agar, on which a disk of perforated Plexiglass is then placed; 24 wells per dish are thus created.

The screening step is carried out by depositing extracts of agar carrying isolated clones resulting from the transformation in the wells of the Walseth Petri dishes (one isolated pure clone/well). This system makes it possible to obtain enzymatic hydrolysis halos since the mycelium remains confined in the well, whereas the cellulolytic enzymes secreted diffuse into the agar. The dishes are incubated at 30° C. for seven days, at the end of which a visual evaluation of the halos is carried out by difference in color between the opaque agar and the transparent hydrolyzed zones.

Figure 2:
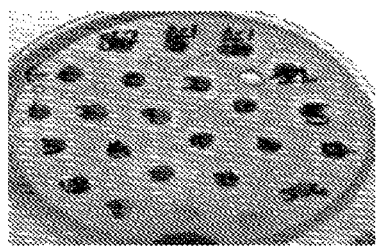
FIG. 2 is a photo showing the hydrolysis halos generated by the enzymes secreted by the pure clones isolated during the screening of *T. reesei* in Walseth Petri dishes.

FIG. 2 illustrates this technique and its discriminating capacity by showing clones of interest identified by comparisons with the two control strains: the CL847ΔCBH1 strain (denoted ΔC1 on the dish) and the CL847 strain from which the cbh1 reference gene has not been deleted (SEQ ID NO: 1).

Thus, any isolated clone of which the halo is smaller than that of CL847ΔCBH1 is discarded, whereas those of which the halo is at least larger than that of CL847ΔCBH1 are retained.

By following this procedure for all of the clones obtained, clones No. 6 and No. 20 resulting from the transformation of the CL847ΔCBH1 strain with the sequence encoding the 130G9 gene (SEQ ID NO: 7) and isolated clone No. 24 resulting from the transformation of the CL847ΔCBH1 strain with the sequence encoding the 453E8 gene (SEQ ID NO: 15) were thus selected and retained.

In order to confirm this choice, the three isolated clones selected were cultured for seven days at 30° C. with shaking at 150 rpm in liquid medium having the following composition:

3.4 g $K_2HPO_4$, 1.68 g $(NH_4)_2SO_4$, 0.12 g $MgSO_4$, 0.6 g cornsteep, 1 ml of trace element solution (30 g/l $FeSO_4.7H_2O$, 9 g/l $Co(NO_3)_2.6H_2O$, 6.4 g/l $MnSO_4.1H_2O$, 8.4 g/l $ZnSO_4.7H_2O$, 0.4 g/l boric acid, 1.04 g/l sodium molybdate, pH adjusted to 1.5 with $H_3PO_4$), 4.64 g maleic acid, 4 g lactose, 4 g Solka Floc cellulose (Nutrafiber, USA) for 1 l of medium. The whole mixture is homogenized using an Ultra Turrax for five minutes. The pH is adjusted to 6.0 with a 3 M KOH solution. The medium obtained is autoclaved at 110° C. for 30 minutes. The phleomycin is added in an amount of 50 µg/ml when the medium is at ambient temperature.

An assay of protein concentration of the extracellular medium is carried out using a DC Protein Assay colorimetric kit (BioRad, California, United States) on the basis of a bovine serum albumin (BSA) standard range. The supernatants are then subjected to two-dimensional electrophoresis as described by Herpoel-Gimbert et al. (Biotechnol Biofuels. 2008 Dec. 23; 1(1):18. doi: 10.1186/1754-6834-1-18), using 7 cm strips, pH 4.0-7.0.

Figure 3:
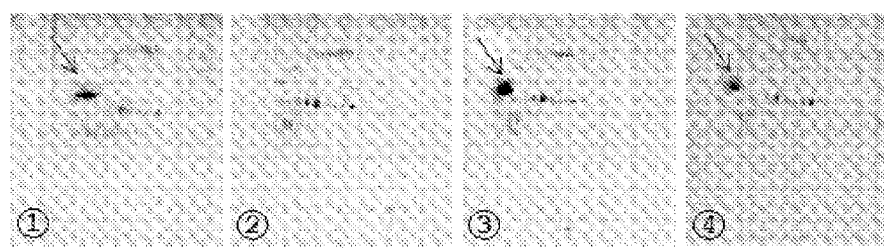
FIG. 3 is a two-dimensional electrophoresis gel comparing the secretomes of the *T. reesei* clones; CL847 reference strain; CL847ΔCBH1 reference strain; isolated pure clones No. 6 and No. 20 of the 130G9 variant (SEQ ID NO: 8).
Figure 4:
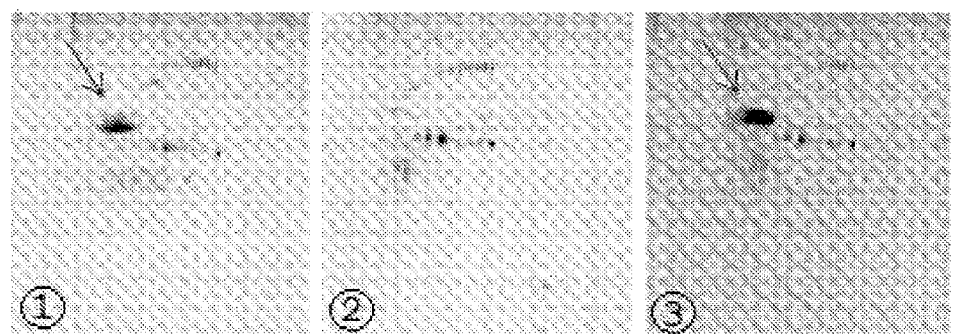
FIG. 4 is a two-dimensional electrophoresis gel comparing the secretomes of the *T. reesei* clones: CL847 reference strain; CL847ΔCBH1 reference strain and isolated pure clone No. 24 of the 453E8 variant (SEQ ID NO: 16).

The protein profiles obtained for clones No. 6 and No. 20 of the 130G9 variant (SEQ ID NO: 8) and for clone No. 24 of the 453E8 variant (SEQ ID NO: 16) are compared with those of the CLN847 and CL847ΔCBH1 reference strains (FIG. 3 and FIG. 4).

The results presented in FIG. 3 and in FIG. 4 show that the intensity of the spots, which correspond to the proteins of the secretome, is similar in each strain. This makes it possible to verify that the expression of these proteins is preserved regardless of the strain. The band indicated by the arrows makes it possible to confirm the presence of CBH1 in these strains, in comparison with the strain having been used for the CL847ΔCBH1 transformations.

The clones selected at the end of these screening steps are referred to as "strains" in the rest of the examples.

Example 6: Production of Enzyme Cocktails

Strains No. 6 and No. 20 having integrated the 130G9 variant (SEQ ID NO: 8) and strain No. 24 having integrated the 453E8 variant (SEQ ID NO: 16), constructed in example 5, were the subject of enzyme productions according to the miniaturized protocol described in patent application FR 2 989 385 and Jourdier et al. (Microb Cell Fact. 2012 May 30; 11:70. doi: 10.1186/1475-2859-11-70). All of the proteins secreted by a given strain constitute its cocktail.

The protein production by the *T. reesei* strains is carried out in two phases: a first batch phase for biomass production and a second fed-batch phase for protein production.

The production is carried out according to the following protocol:

In 250 ml flasks, 55 ml of F45 medium (10 g/l of dipotassium phthalate buffer, pH 6, 4.2 g/l $(NH_4)_2SO_4$, 300 mg/l $MgSO_4.7H_2O$, 150 mg/l $CaCl_2.2H_2O$, 1.5 g/l cornsteep, 0.07% of ortho-phosphoric acid, 5 mg/l $FeSO_4$, 1.4 mg/l $MnSO_4$, 1.4 mg/l $ZnSO_4$, 3.7 mg/l $CoCl_2$ and 12.5 g/l glucose) were inoculated with spores of the respective strains and shaken at 150 rpm and 30° C.

Samples were taken every 24 hours in order to determine the pH and the glucose concentration.

As soon as the glucose concentration is below 3 g/l, the fed-batch phase is launched by adding a solution of 50 g/l lactose and 0.3% $NH_3$ at a flow rate of 40 mg of sugar/g of biomass per hour. Daily samples were taken in order to determine the pH, the dry weight and the protein concentration in the supernatant. After five days of fed-batch culture, the culture is filtered on a 0.45 µm filter and the supernatant is frozen after measuring the protein concentration. Said concentration was measured by the Lowry method using BSA to produce the standard range.

The protein concentrations of the supernatants obtained for the 453E8-24, 130G9-6 and 130G9-20 strains and also the CL847 reference strain are given in table 9.

TABLE 9

Protein concentration of the culture supernatants

| Strain | Protein concentration (g/l) |
|---|---|
| 453E8-24 | 5.3 |
| 130G9-6 | 7.4 |
| 130G9-20 | 5.8 |
| CL847 | 5.2 |

Example 7: Efficiency of the Enzymes Resulting from the L-Shuffling in Lignocellulosic Biomass Hydrolysis According to an SHF Process The reference substrate used is a wheat straw having undergone a vapor-explosion pretreatment (19 bar—3 minutes). The biomass undergoes the explosion after acid impregnation at 0.01% $H_2SO_4$ for 10 hours. It is then washed, adjusted to pH 5, pressed and dried. The characteristics of the straw are given in table 10.

TABLE 10

Composition of the straw used for the hydrolysis tests

| Composition | % w/w |
|---|---|
| WIS | 97.52 |
| Ash content | 5 |
| Cellulose | 51.7 |
| Corrected xylans | 3.57 |
| Hemicellulose | 4.14 |
| Klason lignin (overestimated) | 36.49 |
| Acetyl | 0.6 |

The hydrolyses were carried out at 10% of solids w/w, i.e. an equivalent of 5.4% of cellulose w/w. The WIS (Water Insoluble Solids) content is systematically determined before each series of microhydrolyses. The reference WIS value is 93.7%. The lignocellulosic solids content in the tests was set at 10%, i.e. 5.4% of cellulose.

The protein content is set at 10 mg/g solids, i.e. approximately 19 mg/g cellulose. The enzymatic cocktails were supplied with β-glucosidase activity in an amount of 120±2 IU/g cellulose, by adding SP188 β-glucosidase (Novozymes, Denmark). This addition of β-glucosidase makes it possible to limit the cellobiohydrolase inhibition by cellobiose.

The tests are carried out in Eppendorf tubes with a 2 ml working volume (1 g reactional) containing:

0.11±0.001 g of washed straw substrate;
0.9±0.02 ml of hydrolysis reaction medium composed of 50 mM acetate buffer—pH 4.8 and chloramphenicol (0.05 g/l);
between 0.1 and 0.2±0.02 g of enzymatic cocktail as a function of their protein content.

The enzymatic hydrolyses are carried out at 45±2° C. with vortexing at 900 revolutions per minute in an Eppendorf Thermomixer Comfort.

All the tests are carried out in duplicate with sampling times set at 24, 48 and 96 hours with, for some, samplings at 72 hours.

At each sampling time, the hydrolysates are warmed for five minutes in sacrificed Eppendorf tubes. These tubes are then cooled and centrifuged. The glucose is assayed by HPLC. In parallel, the solid residues of each Eppendorf tube are washed and centrifuged three times before being dried at 105° C. for 24 hours so as to evaluate the WIS. The hydrolysis yield is calculated by taking into account the amount of WIS in the straw used in the hydrolysis tests.

The three cocktails resulting from the 130G9-6, 130G9-20 and 453E8-24 recombinant strains of example 6 were evaluated. A control test is carried out with the CL847 reference cocktail comprising the native CBH1 enzyme also supplemented with β-glucosidase for comparison.

Figure 5:
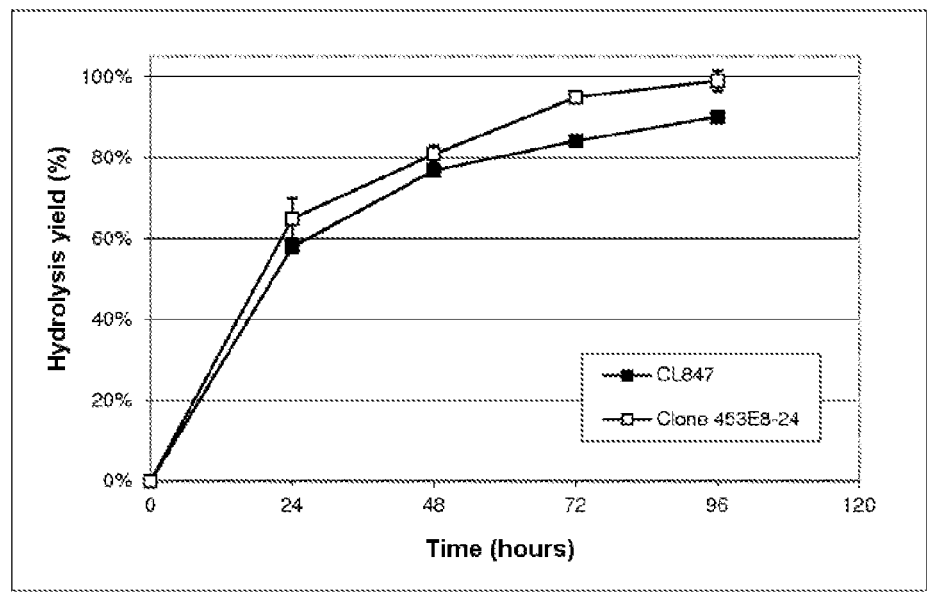
FIG. 5 is a graph presenting the results of SHF for the 453E8-24 cocktail, derived from strain No. 24 expressing the 453E8 variant (SEQ ID NO: 16) and the CL847 reference cocktail supplemented with β-glucosidase.

FIG. 5 gives the hydrolysis results for the 453E8-24 cocktail comprising the 453E8 enzyme (SEQ ID NO: 16).

The results given in FIG. 5 show that the initial rate of hydrolysis of the 453E8-24 cocktail is close to that of the CL847 reference cocktail. The final hydrolysis yield of the 453E8-24 cocktail is greater than that of the CL847 reference cocktail.

Figure 6:
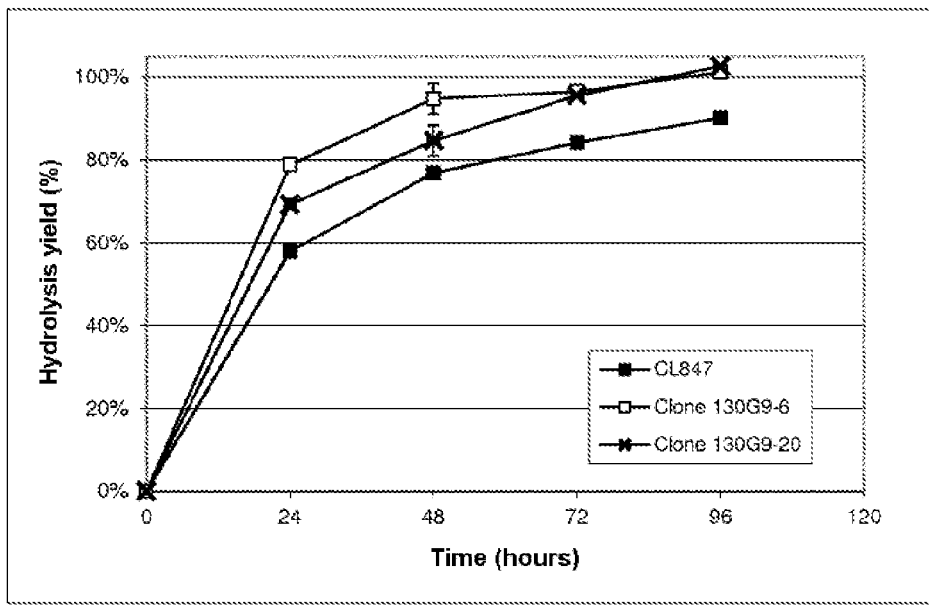
FIG. 6 is a graph presenting the results of SHF for the 130G9-6 and 130G9-20 cocktails derived from strains No. 6 and No. 20 expressing the 130G9 variant (SEQ ID NO: 8) and the CL847 reference cocktail supplemented with β-glucosidase.

FIG. 6 gives the hydrolysis results for the two cocktails 130G9-6 and 130G9-20 resulting from the strains expressing the 130G9 enzyme (SEQ ID NO: 8).

The results given in FIG. 6 show, for the two cocktails 130G9-6 and 130G9-20, that the initial rate of hydrolysis is greater than the rate of hydrolysis of the CL847 reference cocktail for the first 20 hours of reaction. The final hydrolysis yield of the two cocktails 130G9-6 and 130G9-20 is also greater than that of the CL847 reference cocktail.

Example 8: Efficiency of the Enzymes in Lignocellulosic Biomass Hydrolysis According to an SSF Process The substrate used is the same as that described in table 10 of example 7.

The SSFs are carried out in triplicate in laboratory reactors. These reactors consist of the following elements:
a glass flask with a 30 ml working volume;
a polyether ether ketone (PEEK) safety stopper;
a DV-118 one-way valve (Vaplock, United States) fitted through the stopper. The valve is configured so as to open in the outlet direction when the relative pressure in the flask is greater than 70 mbar;
a first hollow polypropylene tube, the lower end of which is equipped with a septum. This tube is fitted through a second tube which passes through the safety stopper;
a flat seal placed between the neck of the flask and the safety stopper.

The principle for using the bioreactors is the following: the $CO_2$ produced during the ethanolic fermentation accumulates in the top located above the reaction medium, leading by accumulation to an increase in the pressure in the bioreactor ($P_G$). When $P_G$ becomes higher than the one-way valve opening pressure ($P_S$), the valve opens to allow an amount of gas to escape, which amount is for example determined by weighing. When $P_G < P_S$, the valve closes again until $P_G$ is higher than $P_S$. Thus, the bioreactor when operating is always pressurized so as to ensure a stable anaerobic environment for the fermentation. The amount of ethanol produced is evaluated by the $CO_2$ production estimated by loss of weight on the basis of the following stoichiometric equation for fermentation of glucose to ethanol:

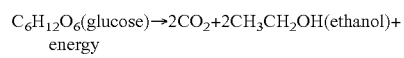

$$C_6H_{12}O_6(\text{glucose}) \rightarrow 2CO_2 + 2CH_3CH_2OH(\text{ethanol}) + \text{energy}$$

The culture medium used for the SSF is an aqueous medium which comprises:
a 50 mM acetate buffer for pH 5;
chloramphenicol at 0.1 g/l;
nutritive medium containing 3 g/l of $KH_2PO_4$, 2 g/l of $(NH_4)_2SO_4$, 0.4 g/l of $MgSO_4.7H_2O$ and 1 g/l of yeast extract.

The SSFs were carried out at 10±0.01% w/w of solids, i.e. an equivalent of 5.4% cellulose w/w for a total reaction weight of 15±0.003 g. The protein content is set at 10±0.01 mg of cellulases per gram of solids, i.e. approximately 19 mg/g of cellulose. The enzymatic cocktails were supplemented with β-glucosidase activity in an amount of 120±2 IU/g cellulose, by adding SP188 β-glucosidase (Novozymes, Denmark).

The yeast for fermentation of the sugars (*Saccharomyces cerevisiae*, Ethanol Red strain, Fermentis, France) is added to the medium so as to obtain a content of 2±0.1 g/kg.

The enzymes and the yeast are added to the bioreactors after one hour of conditioning of the wheat straw pretreated at 35° C. with the culture medium.

The SSF reaction is carried out at a temperature of approximately 35° C., by placing the laboratory bio reactor in an Infors Multitron HT Standard incubator with an orbital rotation speed of 150 revolutions per minute.

Over time, the loss of weight was monitored by weighing the bioreactors. At the end of the reaction, the fermentation must is heated at 100° C. for 5 minutes, cooled and centrifuged to separate the non-hydrolyzed solids from the fermentation liquor. The fermentation liquor is then analyzed by gas chromatography in order to determine its ethanol concentration.

The three cocktails resulting from the 130G9-6, 130G9-20 and 453E8-24 recombinant strains of example 6 were evaluated. An SSF is carried out with the reference cocktail comprising the native CBH1 enzyme also supplemented with β-glucosidase for comparison.

Figure 7:
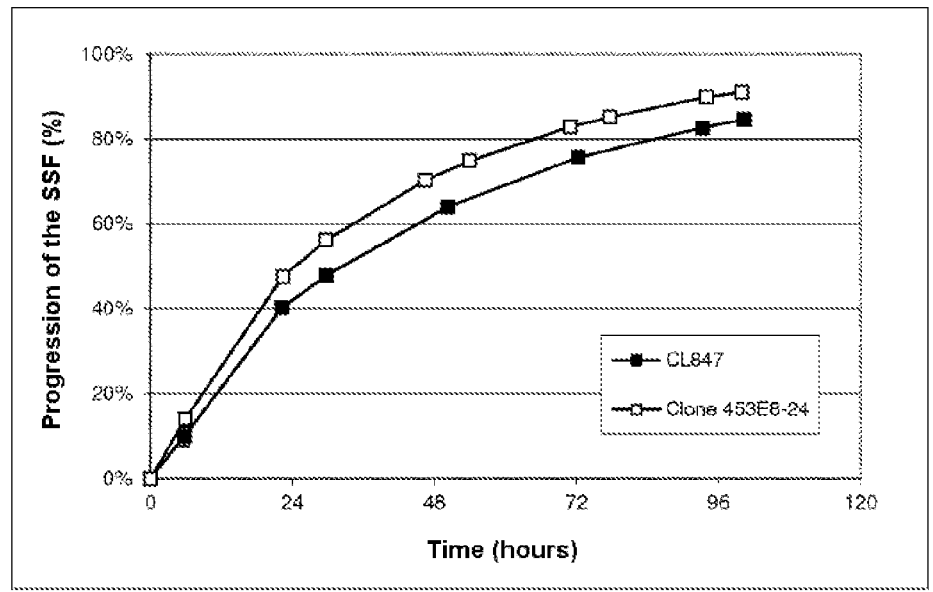
FIG. 7 is a graph presenting the results of SSF for the 453E8-24 cocktail, derived from strain No. 24 expressing the 453E8 variant (SEQ ID NO: 16) and the CL847 reference cocktail supplemented with β-glucosidase.

FIG. 7 gives the results of progression of the SSF for the 453E8-24 cocktail resulting from the strains expressing the 453E8 exoglucanase.

The results given in FIG. 7 show that the ethanol concentration after 100 hours of SSF is equivalent in the fermentation liquor of the 453E8-24 cocktail and in that of the CL847 reference strain.

Figure 8:
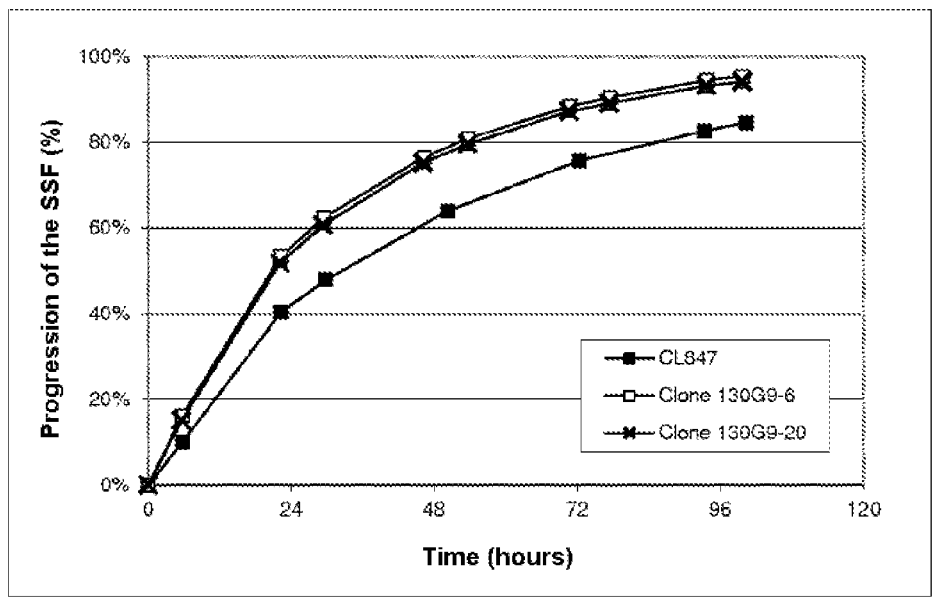
FIG. 8 is a graph presenting the results of SSF for the two cocktails 130G9-6 and 130G9-20 derived from strains No. 6 and No. 20 expressing the 130G9 variant (SEQ ID NO: 8) and the CL847 reference cocktail supplemented with β-glucosidase.

FIG. 8 gives the results of progression of the SSF for the 130G9-6 and 130G9-20 cocktails resulting from the strains expressing the enzyme of the 130G9 clone (SEQ ID NO: 8).

The results given in FIG. 8 show, for the two cocktails 130G9-6 and 130G9-20, that the initial rate of fermentation is greater than that of the CL847 reference cocktail for the first 20 hours of reaction. The final yield of the two cocktails 130G9-6 and 130G9-20 is also greater than that of the CL847 reference cocktail.

The invention claimed is:

1. An isolated or purified polypeptide characterized in that it has exoglucanase activity which is improved by at least 10% at a temperature of 35° C. compared with the exoglucanase activity of the exoglucanase 1 (CBH1) reference protein of SEQ ID NO: 2, said isolated or purified polypeptide comprising an amino acid sequence selected from the group consisting of: SEQ ID NO: 4, SEQ ID NO: 8, SEQ ID NO: 10, and SEQ ID NO: 14.

2. A purified or isolated nucleic acid comprising a nucleotide sequence encoding the polypeptide of claim 1.

3. The purified or isolated nucleic acid of claim 2, wherein the nucleotide sequence is selected from the group consisting of SEQ ID NO: 3, SEQ ID NO: 7, SEQ ID NO: 9, and SEQ ID NO: 13.

4. A vector comprising the nucleic acid of claim 2.

5. An isolated host cell comprising the nucleic acid of claim 2.

6. The isolated host cell of claim 5, wherein the host cell is selected from the group consisting of a *Trichoderma* cell, an *Aspergillus* cell, a *Neurospora* cell, a *Humicola* cell, a *Penicillium* cell, a *Fusarium* cell, a *Thermomonospora* cell, a *Myceliophthora* cell, a *Chrysosporium* cell, a *Bacillus* cell, a *Pseudomonas* cell, an *Escherichia* cell, a *Clostridium* cell, a *Cellulomonas* cell, a *Streptomyces* cell, a *Yarrowia* cell, a *Pichia* cell and a *Saccharomyces* cell.

7. The isolated host cell of claim 5, wherein the host cell is selected from the group consisting of *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

8. An enzymatic composition capable of hydrolyzing lignocellulosic biomass, said enzymatic composition comprising the polypeptide of claim 1.

9. A process for producing an alcohol from lignocellulosic biomass, comprising the following successive steps:
suspending the lignocellulosic biomass in an aqueous phase;
contacting the suspended lignocellulosic biomass with the enzymatic composition of claim 8 to hydrolyze the lignocellulosic biomass and produce a hydrolysate containing glucose;
fermenting the glucose of the hydrolysate with a fermentative microorganism to produce a fermentation must comprising the alcohol; and
separating the alcohol from the fermentation must,
wherein the alcohol is selected from the group consisting of ethanol, butanol, isopropanol, 1,2-propanediol, 1,3-propanediol, 1,4-propanediol, and 2,3-butanediol.

10. A process for producing an alcohol from lignocellulosic biomass, comprising the following successive steps:
suspending the lignocellulosic biomass in an aqueous phase;
contacting the suspended lignocellulosic biomass with the enzymatic composition of claim 8 and a fermentative microorganism to simultaneously hydrolyze the lignocellulosic biomass to produce glucose and ferment the glucose to produce a fermentation must comprising the alcohol; and
separating the alcohol from the fermentation must,
wherein the alcohol is selected from the group consisting of ethanol, butanol, isopropanol, 1,2-propanediol, 1,3-propanediol, 1,4-propanediol, and 2,3-butanediol.

11. The process of claim 10, wherein the enzymatic composition is produced by the fermentative microorganism.

* * * * *